US012760111B2

(12) United States Patent
Sidhu et al.

(10) Patent No.: US 12,760,111 B2
(45) Date of Patent: Oct. 13, 2026

(54) ANTIBODIES AGAINST EGFR AND THEIR USES

(71) Applicant: Erasca, Inc., San Diego, CA (US)

(72) Inventors: Sachdev Sidhu, Toronto (CA); Jarrett Adams, Toronto (CA); Max London, Toronto (CA); Dewald Van Dyk, Clarksburg, MD (US)

(73) Assignee: ERASCA, INC., San Diego, CA (US)

( * ) Notice: Subject to any disclaimer, the term of this patent is extended or adjusted under 35 U.S.C. 154(b) by 314 days.

(21) Appl. No.: 18/573,339

(22) PCT Filed: Jun. 24, 2022

(86) PCT No.: PCT/US2022/034990
§ 371 (c)(1),
(2) Date: Dec. 21, 2023

(87) PCT Pub. No.: WO2022/272128
PCT Pub. Date: Dec. 29, 2022

(65) Prior Publication Data

US 2024/0383988 A1 Nov. 21, 2024

Related U.S. Application Data

(60) Provisional application No. 63/214,596, filed on Jun. 24, 2021.

(51) Int. Cl.
*C07K 16/28* (2006.01)

(52) U.S. Cl.
CPC ...... *C07K 16/2863* (2013.01); *C07K 2317/24* (2013.01); *C07K 2317/31* (2013.01)

(58) Field of Classification Search
None
See application file for complete search history.

(56) References Cited

U.S. PATENT DOCUMENTS

| | | | | |
|---|---|---|---|---|
| 8,642,745 | B2 | 2/2014 | Arathoon et al. | |
| 2007/0009972 | A1 | 1/2007 | Chao et al. | |
| 2014/0322756 | A1 | 10/2014 | Arathoon et al. | |
| 2025/0043012 | A1* | 2/2025 | Sidhu ................. | C07K 16/2863 |

FOREIGN PATENT DOCUMENTS

| | | | |
|---|---|---|---|
| WO | WO-2009089004 | A1 | 7/2009 |
| WO | WO-2018152634 | A1 | 8/2018 |
| WO | WO-2021160138 | A1 | 8/2021 |
| WO | WO-2022272128 | A1 | 12/2022 |
| WO | WO-2023172981 | A1 | 9/2023 |

OTHER PUBLICATIONS

Al-Lazikani, B, et al., Standard Conformations for the Canonical Structures of Immunoglobulins. Journal of Molecular Biology 273(4):927-948 (1997).

Altschul, et al. Basic Local Alignment Search Tool. Journal of Molecular Biology 215(3):403-410 (1990).

Aratani et al., Overexpression of EGFR as an Independent Prognostic Factor in Adenocarcinoma of the Esophagogastric Junction. Anticancer research 37(6):3129-3135 (2017).

Bethune et al., Epidermal growth factor receptor (EGFR) in lung cancer: an overview and update. Journal of Thoracic Disease 2(1):48-51 (2010).

Bogen et al., Expeditious generation of biparatopic common light chain antibodies via chicken immunization and yeast display screening. Front Immunol. 11:606878 ( 2020).

Brinkmann et al. The making of bispecific antibodies. Mabs 9(2):182-212 (2017).

Clackson et al. Making antibody fragments using phage display libraries. Nature 352(6336):624-628 (1991).

Dawson et al., Epidermal Growth Factor Receptor Dimerization and Activation Require Ligand-induced Conformational Changes in the Dimer Interface. Molecular and cellular biology 25(17):7734-7742 (2005).

Filmus et al., MDA-468, a human breast cancer cell line with a high number of epidermal growth factor (EGF) receptors, has an amplified EGF receptor gene and is growth inhibited by EGF. Biochemical and biophysical research communications 128(2):898-905 (1985).

Foncillas et al., Distinguishing Features of Cetuximab and Panitumumab in Colorectal Cancer and Other Solid Tumors. Frontiers in oncology 9:849 (2019).

Hashmi et al., Prognostic significance of epidermal growth factor receptor (EGFR) over expression in urothelial carcinoma of urinary bladder. BMC urology 18(1):59 (2018).

Honegger, A et al., Yet Another Numbering Scheme for Immunoglobulin Variable Domains: An Automatic Modeling and Analysis Tool. Journal of Molecular Biology 309(3):657-670 (2001).

Kabat et al.: Sequences of Proteins of Immunological Interest. NIH Pub. No. 91-3242. Public Health Service, National Institutes of Health. 1:647-669 (1991).

Karlin, S et al., Methods for assessing the statistical significance of molecular sequence features by using general scoring schemes. PNAS USA 87(6):2264-2268 (1990).

Khan et al., Biparatopic Targeting of Epidermal Growth Factor Receptor Positive Breast Cancer Cells using Domain I/II and Domain III Specific Antibody Conjugates. Journal of Medical Imaging and Radiation Sciences 50(4 Supp. 1):S98-S99 (2019).

Lefranc, Marie-Paule, et al., IMGT Unique Numbering for Immunoglobulin and T Cell Receptor Variable Domains and Ig Superfamily V-like Domains. Developmental & Comparative Immunology 27(1):55-77 (2003).

Li et al. Cell culture processes for monoclonal antibody production. Mabs. 2(5):466-477 (2010).

(Continued)

*Primary Examiner* — Misook Yu
(74) *Attorney, Agent, or Firm* — WILSON SONSINI GOODRICH & ROSATI

(57) ABSTRACT

Described herein are antibodies that bind EGFR domain II and/or Domain III. Also described are bispecific antibodies that bind domain II and domain II of EGFR. Also described are methods and uses for treating cancer.

21 Claims, 6 Drawing Sheets

Specification includes a Sequence Listing.

(56) References Cited

OTHER PUBLICATIONS

Li et al., Overexpression of Epidermal Growth Factor Receptor (EGFR) and HER-2 in Bladder Carcinoma and Its Association with Patients' Clinical Features. Medical Science Monitor: International Medical Journal of Experimental and Clinical Research 24:7178-7185 (2018).
Maccallum, Robert M, et al., Antibody-Antigen Interactions: Contact Analysis and Binding Site Topography. Journal of Molecular Biology 262(5):732-745 (1996).
Nevoltris et al., Conformational nanobodies reveal tethered epidermal growth factor receptor involved in EGFR/ErbB2 predimers. ACS Nano 9(2):1388-1399 (2015).
PCT/US2022/034990 International Search Report and Written Opinion dated Oct. 20, 2022.
PCT/US2023/063986 International Search Report and Written Opinion dated Jun. 15, 2023.
Portolano, S, et al., Lack of Promiscuity in Autoantigen-specific H and L Chain Combinations as Revealed by Human H and L Chain "roulette". Journal of Immunology 150(3):880-887 (1993).
Roovers et al., A biparatopic anti-EGFR nanobody efficiently inhibits solid tumour growth. Int J Cancer. 129(8):2013-2024 (2011).
Whitelegg et al. WAM: an improved algorithm for modelling antibodies on the Web. Protein Eng. 13:819-24 (2000).
Wieduwilt et al., The Epidermal Growth Factor Receptor Family: Biology Driving Targeted Therapeutics. Cellular and Molecular Life Sciences : CMLS 65(10):1566-1584 (2008).
Karlin, S. et al. Applications and statistics for multiple high-scoring segments in molecular sequences. PNAS USA 90(12):5873-5877 (1993).
Kindt. Thomas J. et al. Chapter 4: Antibodies: Structure and Function,Sixth Edition. Kuby Immunology pp. 91 (2007).

* cited by examiner

| Ab | CDR-H1 | CDR-H2 | CDR-H3 | $k_{on}$ | $k_{off}$ | $K_D \pm$ SE |
|---|---|---|---|---|---|---|
| | 30 35 36 37 38 39 | 55 56 57 58 59 62 63 64 65 66 | 107 108 109 110 111.1 111.2 111.3 111.4 111.5 111.6 112.6 112.5 112.4 112.3 112.2 112.1 113 114 115 | $10^5$ ($s^{-1}M^{-1}$) | $10^{-4}$ ($s^{-1}$) | (nM) |
| ER-2 | L Y Y S S M | S I S P Y Y G Y T S | Y Y H F S W H W S S F G G S Y Y P G M | 0.7 | 13 | 20 |
| ER-2a | V Y Y A A M | S I S P Y Y G Y T S | Y Y H F S W H W S S F G G S Y Y P G M | 2.2 | 0.61 | 0.28 ± 1.1 |
| ER-2b | I Y Y A A M | F I S P Y Y S Y T S | Y F H S S W Y E S S S P R A Y Y P G M | 2.8 | 0.5 | Y |
| ER-3 | L Y S Y S M | Y I S P S S G S T Y | H W Y Y Y P S - - - - - - Y Y W G G F | 5.8 | 84 | 14 |
| ER-3a | L Y S Y S M | S V S P S S G S T Y | H W H V Y P S - - - - - - Y Y W G G F | 1.5 | 0.49 | S |
| ER-3b | I Y S F S I | S I S P S A G S T Y | H W H V Y P S - - - - - - Y Y W G G M | 2.9 | 1.6 | S |

FIG. 2

ANTIBODIES AGAINST EGFR AND THEIR USES

CROSS REFERENCE TO RELATED APPLICATION(S)

This application is a § 371 U.S. National Stage Entry of International Application No. PCT/US2022/034990, filed Jun. 24, 2022, which claims the benefit of U.S. Provisional Ser. No. 63/214,596, filed on Jun. 24, 2021, all of which are incorporated by reference herein in their entirety.

BACKGROUND

The epidermal growth factor receptor (EGFR), a member of the ErbB family of receptor tyrosine kinases (RTKs), directs proliferation and differentiation of many different tissues. See Wieduwilt M J & Moasser M M (2008) The epidermal growth factor receptor family: biology driving targeted therapeutics. *Cell Mol Life Sci* 65(10):1566-1584. Overexpression of EGFR occurs in numerous epithelial tumors and is associated with poor clinical outcome. See e.g., Aratani K, et al. (2017) Overexpression of EGFR as an Independent Prognostic Factor in Adenocarcinoma of the Esophagogastric Junction. *Anticancer Res* 37(6):3129-3135. Bethune G, Bethune D, Ridgway N, & Xu Z (2010) Epidermal growth factor receptor (EGFR) in lung cancer: an overview and update. *J Thorac Dis* 2(1):48-51; Hashmi A A, et al. (2018) Prognostic significance of epidermal growth factor receptor (EGFR) over expression in urothelial carcinoma of urinary bladder. *BMC Urol* 18(1):59; Li W, et al. (2018) Overexpression of Epidermal Growth Factor Receptor (EGFR) and HER-2 in Bladder Carcinoma and Its Association with Patients' Clinical Features. *Med Sci Monit* 24:7178-7185. To date, four anti-EGFR antibodies have been approved for human therapy and several others are in clinical trials. However, use of even the most popular therapeutic antibodies, Cetuximab (CTX) and Panitumumab (PTMB), is limited to a small subset of EGFR-positive tumors. See Garcia-Foncillas J, et al. (2019) Distinguishing Features of Cetuximab and Panitumumab in Colorectal Cancer and Other Solid Tumors. *Front Oncol* 9:849.

SUMMARY

Described herein are EGFR binding antibodies. These antibodies bind to domain II and/or domain III of human EGFR. Also described are bispecific antibodies that are capable of binding both domain II and domain III of EGFR. Such antibodies advantageously expand the therapeutic utility of targeting EGFR beyond previous EGFR antibodies and allow inhibition of EGFR signaling in the "open" confirmation, which allows the antibodies to be more effective and effective against a broader range of cancers and tumors. Accordingly, also described herein are methods and uses of the antibodies in treating cancers and tumors.

In one aspect described herein is an antibody or antigen binding fragment thereof comprising: a) a heavy chain complementarity determining region 1 (HCDR1) comprising an amino acid sequence set forth in SEQ ID NO: 17; b) a heavy chain complementarity determining region 2 (HCDR2) comprising an amino acid sequence set forth in SEQ ID NO: 18; c) a heavy chain complementarity determining region 3 (HCDR3) comprising an amino acid sequence set forth in any one of SEQ ID NOs: 23 to 38; d) a light chain complementarity determining region 1 (LCDR1) comprising an amino acid sequence set forth in any one of SEQ ID NOs: 4 or 5; e) a light chain complementarity determining region 2 (LCDR2) comprising an amino acid sequence set forth in SEQ ID NO: 6; and/or f) a light chain complementarity determining region 3 (LCDR3) comprising an amino acid sequence set forth in SEQ ID NO: 7; wherein the antibody binds to EGFR domain II. In certain embodiments, the antibody or antigen binding fragment thereof is chimeric or humanized. In certain embodiments, the antibody or antigen binding fragment thereof is an IgG antibody. In certain embodiments, the antibody or antigen binding fragment thereof is a Fab, $F(ab)_2$, a single-domain antibody, or a single chain variable fragment (scFv). In certain embodiments, the antibody or antigen binding fragment thereof is a multispecific antibody. In certain embodiments, the antibody or antigen binding fragment thereof is a bispecific antibody. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 16 or 20; and wherein the immunoglobulin light chain comprises an amino acid sequence at least about 90%, 95%, 97%, 99%, or 100% identical to that set forth in SEQ ID NO: 2 or 3. In certain embodiments, the antibody or antigen binding fragment binds to EGFR with a KD of 50 nanomolar or less. In certain embodiments, the antibody or antigen binding fragment binds to EGFR with a KD of 10 nanomolar or less.

In another aspect described herein is an EGFR domain III binding antibody comprising: a) a heavy chain complementarity determining region 1 (HCDR1) comprising an amino acid sequence set forth in SEQ ID NO: 52; b) a heavy chain complementarity determining region 2 (HCDR2) comprising an amino acid sequence set forth in SEQ ID NO: 53; c) a heavy chain complementarity determining region 3 (HCDR3) comprising an amino acid sequence set forth in any one of SEQ ID NOs: 54 to 60; d) a light chain complementarity determining region 1 (LCDR1) comprising an amino acid sequence set forth in any one of SEQ ID NOs: 4 or 5; e) a light chain complementarity determining region 2 (LCDR2) comprising an amino acid sequence set forth in SEQ ID NO: 6; and/or f) a light chain complementarity determining region 3 (LCDR3) comprising an amino acid sequence set forth in SEQ ID NO: 7; wherein the antibody binds to EGFR domain III. In certain embodiments, the antibody or antigen binding fragment thereof is chimeric or humanized. In certain embodiments, the antibody or antigen binding fragment thereof is an IgG antibody. In certain embodiments, the antibody or antigen binding fragment thereof is a Fab, $F(ab)_2$, a single-domain antibody, or a single chain variable fragment (scFv). In certain embodiments, the antibody or antigen binding fragment thereof is a multispecific antibody. In certain embodiments, the antibody or antigen binding fragment thereof is a bispecific antibody. In certain embodiments, the antibody or antigen binding fragment thereof comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 51; and wherein the immunoglobulin light chain comprises an amino acid sequence at least about 90%, 95%, 97%, 99%, or 100% identical to that set forth in SEQ ID NO: 2 or 3. In certain embodiments, the antibody or antigen binding fragment binds to EGFR with a KD of 500 nanomolar or less. In certain embodiments, the antibody or antigen binding fragment binds to EGFR with a KD of 300 nanomolar or less.

Also described herein in one aspect is a bispecific antibody or antigen binding fragment thereof that binds to EGFR domain II and EGFR domain III. In certain embodiments, the bispecific antibody comprises an EGFR domain II binding moiety, wherein the EGFR domain II binding moiety comprises: (a) a heavy chain complementarity determining region 1 (HCDR1) comprising an amino acid sequence set forth in any one of SEQ ID NOs: 17; (b) a heavy chain complementarity determining region 2 (HCDR2) comprising an amino acid sequence set forth in any one of SEQ ID NOs: 18; (c) a heavy chain complementarity determining region 3 (HCDR3) comprising an amino acid sequence set forth in any one of SEQ ID NOs: 23 to 38; (d) a light chain complementarity determining region 1 (LCDR1) comprising an amino acid sequence set forth in any one of SEQ ID NOs: 4 or 5; (e) a light chain complementarity determining region 2 (LCDR2) comprising an amino acid sequence set forth in any one of SEQ ID NOs: 6; and/or (f) a light chain complementarity determining region 3 (LCDR3) comprising an amino acid sequence set forth in any one of SEQ ID NOs: 7. In certain embodiments, the bispecific antibody comprises an EGFR domain III binding moiety, wherein the EGFR domain III antigen binding moiety comprises: (a) a heavy chain complementarity determining region 1 (HCDR1) comprising an amino acid sequence set forth in any one of SEQ ID NOs: 52; (b) a heavy chain complementarity determining region 2 (HCDR2) comprising an amino acid sequence set forth in any one of SEQ ID NOs: 53; (c) a heavy chain complementarity determining region 3 (HCDR3) comprising an amino acid sequence set forth in any one of SEQ ID NOs: 54 to 60; (d) a light chain complementarity determining region 1 (LCDR1) comprising an amino acid sequence set forth in any one of SEQ ID NOs: 4 or 5; € a light chain complementarity determining region 2 (LCDR2) comprising an amino acid sequence set forth in any one of SEQ ID NOs: 6; and/or (f) a light chain complementarity determining region 3 (LCDR3) comprising an amino acid sequence set forth in any one of SEQ ID NOs: 7. Also described herein, is a bispecific antibody or antigen binding fragment thereof comprising an EGFR domain II and an EGFR domain III binding moiety, wherein the EGFR domain II binding moiety comprises: a) a heavy chain complementarity determining region 1 (HCDR1) comprising an amino acid sequence set forth in any one of SEQ ID NOs: 17; b) a heavy chain complementarity determining region 2 (HCDR2) comprising an amino acid sequence set forth in any one of SEQ ID NOs: 18; c) a heavy chain complementarity determining region 3 (HCDR3) comprising an amino acid sequence set forth in any one of SEQ ID NOs: 23 to 38; d) a light chain complementarity determining region 1 (LCDR1) comprising an amino acid sequence set forth in any one of SEQ ID NOs: 4 or 5; e) a light chain complementarity determining region 2 (LCDR2) comprising an amino acid sequence set forth in any one of SEQ ID NOs: 6; and f) a light chain complementarity determining region 3 (LCDR3) comprising an amino acid sequence set forth in any one of SEQ ID NOs: 7; and wherein the EGFR domain III antigen binding moiety comprises: g) a heavy chain complementarity determining region 1 (HCDR1) comprising an amino acid sequence set forth in any one of SEQ ID NOs: 52; h) a heavy chain complementarity determining region 2 (HCDR2) comprising an amino acid sequence set forth in any one of SEQ ID NOs: 53; i) a heavy chain complementarity determining region 3 (HCDR3) comprising an amino acid sequence set forth in any one of SEQ ID NOs: 54 to 60; j) a light chain complementarity determining region 1 (LCDR1) comprising an amino acid sequence set forth in any one of SEQ ID NOs: 4 or 5; k) a light chain complementarity determining region 2 (LCDR2) comprising an amino acid sequence set forth in any one of SEQ ID NOs: 6; and/or l) a light chain complementarity determining region 3 (LCDR3) comprising an amino acid sequence set forth in any one of SEQ ID NOs: 7. In certain embodiments, the bispecific antibody or antigen binding fragment thereof is chimeric or humanized. In certain embodiments, the bispecific antibody or antigen binding fragment thereof comprises an IgG constant region. In certain embodiments, the EGFR domain II binding moiety and the EGFR domain III binding moiety comprises a common immunoglobulin light chain, wherein the common immunoglobulin light chain comprises an amino acid sequence at least about 90%, 95%, 97%, 99%, or 100% identical to that set forth in SEQ ID NO: 2 or 3. In certain embodiments, the EGFR domain II binding moiety comprises an EGFR domain II binding immunoglobulin heavy chain, wherein the EGFR domain II binding immunoglobulin heavy chain comprises an amino acid sequence at least about 90%, 95%, 97%, 99%, or 100% identical to that set forth in SEQ ID NO: 16 or 20. In certain embodiments, the EGFR domain III binding moiety comprises an EGFR domain III binding immunoglobulin heavy chain, wherein the EGFR domain III binding immunoglobulin heavy chain comprises an amino acid sequence at least about 90%, 95%, 97%, 99%, or 100% identical to that set forth in SEQ ID NO: 51. In certain embodiments, the EGFR domain II binding immunoglobulin heavy chain and the EGFR domain III binding immunoglobulin heavy chain, comprise an IgG constant region; the common immunoglobulin light chain is associated with the EGFR domain II binding immunoglobulin heavy chain and the EGFR domain III binding immunoglobulin heavy chain; and the EGFR domain II binding immunoglobulin heavy chain and the EGFR domain III binding immunoglobulin heavy chain associate with each other. In certain embodiments, the IgG constant region of the EGFR domain II binding immunoglobulin heavy chain and the EGFR domain III binding immunoglobulin heavy chain differ at one or more amino acid positions such that the heterodimerization of the EGFR domain II binding immunoglobulin heavy chain and the EGFR domain III binding immunoglobulin heavy chain is favored. In certain embodiments, one of the EGFR domain II binding immunoglobulin heavy chain and the EGFR domain III binding immunoglobulin heavy chain comprises a T366W substitution (EU numbering) and the other of the EGFR domain II binding immunoglobulin heavy chain or the EGFR domain III binding immunoglobulin heavy chain comprises a T366S/L368A/Y407V substitution (EU numbering), such that the heterodimerization of the EGFR domain II binding immunoglobulin heavy chain and the EGFR domain III binding immunoglobulin heavy chain is favored. In certain embodiments, one of the EGFR domain II binding immunoglobulin heavy chain and the EGFR domain III binding immunoglobulin heavy chain comprises one or more substitutions selected from Q347M, Y348F, T350D, T389W, L368M (EU numbering) and the other of the EGFR domain II binding immunoglobulin heavy chain or the EGFR domain III binding immunoglobulin heavy chain comprises one or more substitutions selected from S354I, E357L, K359S, T366S, L368A, and Y412V (EU numbering), such that the heterodimerization of the EGFR domain II binding immunoglobulin heavy chain and the EGFR domain III binding immunoglobulin heavy chain is favored. In certain embodiments, one of the EGFR domain II binding immunoglobulin heavy chain and the EGFR domain III binding immunoglobulin heavy chain comprises an amino acid sequence at least about 90%, 95%, 97%, 98%, 99% or is 100% identical to SEQ ID NO: 61 and the other of the EGFR domain II binding immunoglobulin heavy chain or the EGFR domain III binding immunoglobulin heavy chain comprises an amino acid sequence at least about 90%, 95%, 97%, 98%, 99% or is 100% identical to SEQ ID NO: 62, such that the heterodimerization of the EGFR domain II binding immunoglobulin heavy chain and the EGFR domain III binding immunoglobulin heavy chain is favored. In certain embodiments, the bispecific antibody or antigen binding fragment binds to EGFR with a KD of 100 nanomolar or less. In certain embodiments, the bispecific antibody or antigen binding fragment binds to EGFR with a KD of 50 nanomolar or less. In certain embodiments, the bispecific antibody or antigen binding fragment binds to EGFR with a KD of 10 nanomolar or less. In certain embodiments, the bispecific antibody or antigen binding fragment binds to the open confirmation of EGFR.

Also described herein is an antibody, bispecific antibody or antigen binding fragment thereof of that bind the same epitope or overlaps in binding with an antibody or bispecific antibody or antigen binding fragment thereof disclosed herein.

Also described herein is an antibody, bispecific antibody or antigen binding fragment thereof of that competes for binding with the antibody, bispecific antibody or antigen binding fragment thereof disclosed herein.

Also described herein is a composition comprising an antibody, bispecific antibody or antigen binding fragment thereof described herein and a pharmaceutically acceptable diluent, carrier, or excipient.

Also described herein is a nucleic acid or plurality of nucleic acids comprising a polynucleotide sequence encoding an antibody, bispecific antibody or antigen binding fragment thereof described herein.

Also described herein is a cell comprising the nucleic acid or plurality of nucleic acids comprising a polynucleotide sequence encoding an antibody, bispecific antibody or antigen binding fragment thereof described herein. In certain embodiments, the cell is a eukaryotic cell. In certain embodiments, the eukaryotic cell is a mammalian cell. In certain embodiments, the cell is a prokaryotic cell.

Also described herein is the use of the antibody, bispecific antibody or antigen binding fragment thereof described herein in a method of treating cancer or tumor in an individual. In certain embodiments, the cancer or tumor is a solid tissue cancer or tumor. In certain embodiments, the cancer or tumor express EGFR. In certain embodiments, the cancer or tumor over expresses EGFR. In certain embodiments, the cancer or tumor comprises colorectal cancer. In certain embodiments, the cancer or tumor comprises head and neck cancer.

Also described herein is a method of treating an individual afflicted with a cancer or a tumor comprising administering to the individual afflicted with the cancer or the tumor the antibody, bispecific antibody or antigen binding fragment described herein, thereby treating the cancer or the tumor. In certain embodiments, the cancer or tumor is a solid tissue cancer or tumor. In certain embodiments, the cancer or tumor express EGFR. In certain embodiments, the cancer or tumor over expresses EGFR. In certain embodiments, the cancer or tumor comprises colorectal cancer. In certain embodiments, the cancer or tumor comprises head and neck cancer. In certain embodiments, the cancer or tumor comprises non-small cell lung cancer (NSCLC).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 illustrates heavy chain CDR sequences and kinetic affinities of antibodies targeting EGFR. The heavy chain CDR sequences are ER-2 (SEQ ID Nos 9-11), ER-2a (SEQ ID Nos 13-15), ER-2b (SEQ ID Nos 17-19), ER-3 (SEQ ID Nos 40-42), ER-3a (SEQ ID Nos 44-46), and ER-3b SEQ ID Nos 48-50).

FIG. 3D illustrates inhibition of EGFR signaling for clones 2a and 3a.

DETAILED DESCRIPTION

Figure 1:
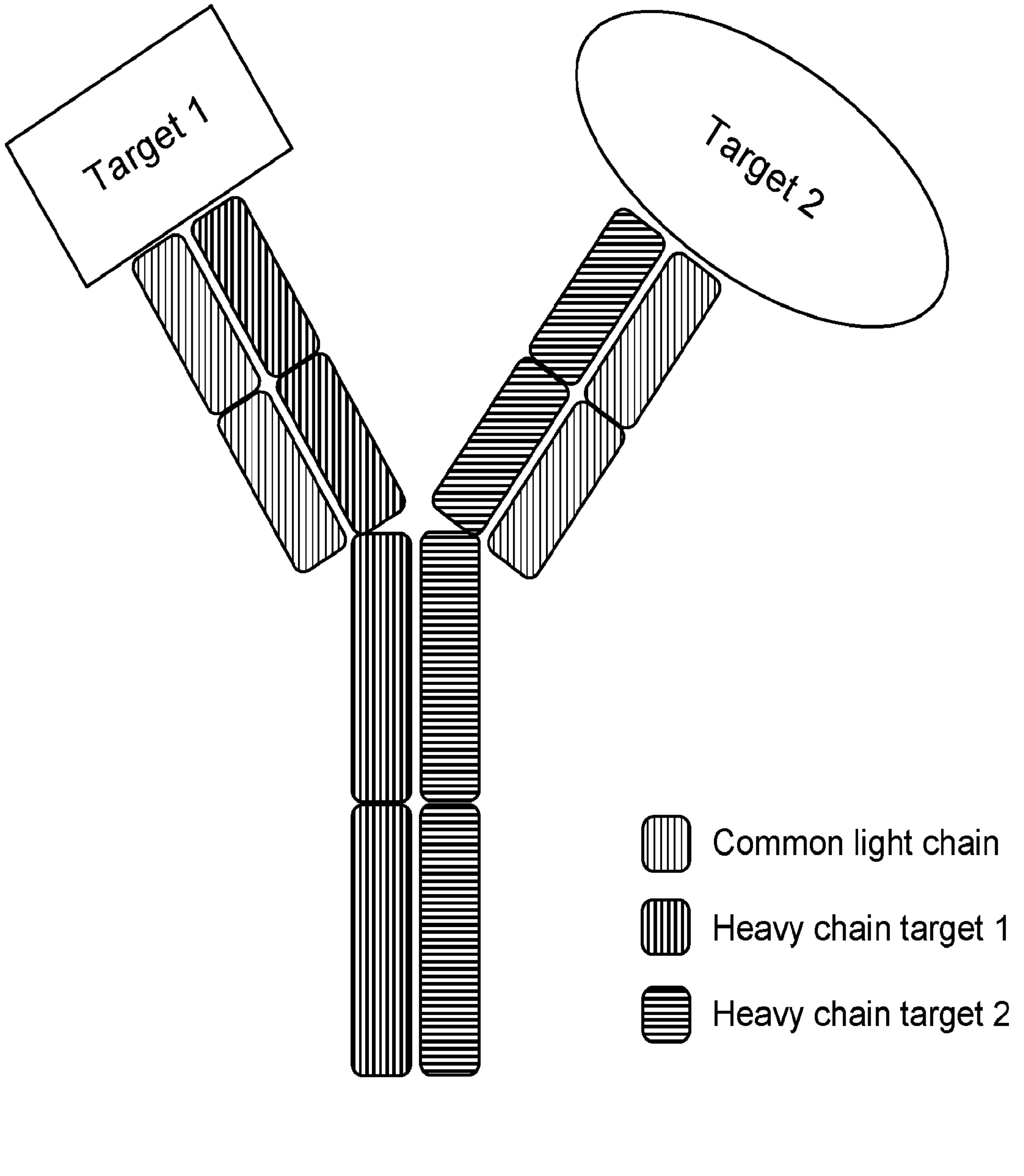
FIG. 1 shows a certain non-limiting embodiment of a common light chain bispecific antibody (not to scale).

The terms “cancer” and “tumor” refer to the physiological condition in mammals characterized by deregulated cell growth.

The term “EGFR” or “Epidermal growth factor receptor” refers to the protein product of the EGFR gene. In certain embodiments, the EGFR gene is a human EGFR gene. In certain embodiments, the EGFR gene is a mammalian EGFR gene. In certain embodiments, the EGFR gene is a simian EGFR gene. In certain embodiments, the EGFR gene is a mouse EGFR gene. In certain embodiments, the EGFR gene is a rat EGFR gene. An exemplary Human EGFR sequence is in SEQ ID NO 1. EGFR proteins of the present disclosure include naturally occurring variants and naturally occurring post-translational modifications able to be bound by the antibodies described herein.

The EGFR ectodomain (ECD) is comprised of four structured domains and exists in at least two distinct conformations. The domains of EGFR comprise Domain I (amino acids 1-165), domain II (amino acids 165-310), domain III (amino acids 310-480), and domain IV (amino acids 480-

620). In the absence of ligand and at low concentrations, domain II interacts with domain IV and tethers the ECD in a closed conformation. Upon ligand binding at an interface between domains III and IV, the ECD adapts a radically different open conformation, which frees a dimerization arm in domain II to interact with another EGFR or other ErbB family member to form active signaling dimers. See Dawson J P, et al. (2005). Epidermal growth factor receptor dimerization and activation require ligand-induced conformational changes in the dimer interface. *Mol Cell Biol* 25 (17):7734-7742.

As used herein the term "individual," "patient," or "subject" refers to individuals diagnosed with, suspected of being afflicted with, or at-risk of developing at least one disease for which the described compositions and method are useful for treating. In certain embodiments, the individual is a mammal. In certain embodiments, the mammal is a mouse, rat, rabbit, dog, cat, horse, cow, sheep, pig, goat, llama, alpaca, or yak. In certain embodiments, the individual is a human.

As used herein, the term "about" used to modify a specific number refers to that number plus or minus 10% of that number. The term "about" modifying a range refers to that range minus 10% of its lowest value and plus 10% of its greatest value.

As used herein, the terms "treatment" or "treating" are used in reference to a pharmaceutical or other intervention regimen used for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made. Skilled artisans will recognize that given a population of potential individuals for treatment not all will respond or respond equally to the treatment. Such individuals are considered treated if administered the compositions including the pharmaceutical compositions described herein.

The term "antibody" herein is used in the broadest sense and includes multivalent or bispecific antibodies and monoclonal antibodies, including intact antibodies and functional (antigen-binding) antibody fragments thereof, including fragment antigen binding (Fab) fragments, $F(ab')_2$ fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. Antibodies as described herein also comprise multispecific or bispecific binding molecules that incorporate one or more complementarity determining regions that contribute to specific binding to a given target antigen. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD. The antibody can comprise a human IgG1 constant region. The antibody can comprise a human IgG4 constant region.

Among the provided antibodies are multispecific or multivalent antibodies (for example, bispecific antibodies and polyreactive antibodies) and antibody fragments thereof. The antibodies include antibody-conjugates and molecules comprising the antibodies, such as chimeric molecules. Thus, an antibody includes, but is not limited to, full-length and native antibodies, as well as fragments and portion thereof retaining the binding specificities thereof, such as any specific binding portion thereof including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, $F(ab')_2$, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A monoclonal antibody can comprise a human IgG1 constant region or a human IgG4 constant region.

The terms "complementarity determining region," and "CDR," which are synonymous with "hypervariable region" or "HVR," are known in the art and refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273, 927-948 ("Chothia" numbering scheme); MacCallum et al., *J. Mol. Biol.* 262:732-745 (1996), "Antibody-antigen interactions: Contact analysis and binding site topography," *J. Mol. Biol.* 262, 732-745." ("Contact" numbering scheme); Lefranc M P et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Plückthun A, "Yet another numbering scheme for immunoglobulin variable domains: an automatic modeling and analysis tool," *J Mol Biol,* 2001 Jun. 8; 309(3):657-70, ("Aho" numbering scheme); and Whitelegg N R and Rees A R, "WAM: an improved algorithm for modelling antibodies on the WEB," *Protein Eng.* 2000 December; 13(12):819-24 ("AbM" numbering scheme. In certain embodiments, the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs (See e.g., Kindt et al. Kuby *Immunology,* 6th ed., W. H. Freeman and Co., page 91(2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (See e.g., Portolano et al., *J. Immunol.* 150:880-887 (1993); Clarkson et al., *Nature* 352:624-628 (1991)).

Among the provided antibodies are antibody fragments. An "antibody fragment" can refer to a molecule other than an intact antibody that comprises a portion of an intact antibody that binds the antigen to which the intact antibody binds. Examples of antibody fragments include, but are not limited to, Fv, Fab, Fab', Fab'-SH, $F(ab')_2$: diabodies; linear antibodies; single-chain antibody molecules (e.g. scFv or sFv); and multispecific antibodies formed from antibody fragments. In particular embodiments, the antibodies are single-chain antibody fragments comprising a variable heavy chain region and/or a variable light chain region, such as scFvs. Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., polypeptide linkers, and/or those that are not produced by enzyme digestion of a naturally-occurring intact antibody.

Herein a molecule, peptide, polypeptide, antibody, or antibody fragment can be referred to as "bispecific" or "dual-specific" including grammatical equivalents. A bispecific molecule possesses the ability to specifically bind to at least two structurally distinct targets. The specific binding may be the result of two distinct binding moieties that are structurally distinct at the molecular level, including but not limited to distinct non-identical amino acid sequences; or a single binding moiety that is able to specifically bind to two structurally distinct targets with high affinity (e.g., with a KD less than about $1\times10^{-6}$). A molecule, peptide, polypeptide, antibody, or antibody fragment referred to as "multi-specific" refers to a molecule that possesses the ability to specifically bind to at least three structurally distinct targets.

A "bispecific antibody" including grammatical equivalents refers to a bispecific molecule that preserves at least one fragment of an antibody able to specifically bind a target, for example, a variable region, heavy or light chain, or one or more complementarity determining regions from an antibody molecule. A "multi-specific antibody" including grammatical equivalents refers to a multi-specific molecule that preserves at least one fragment of an antibody able to specifically bind with a target, for example, a variable region, heavy or light chain, or complementarity determining region from an antibody molecule. A "common light chain bispecific antibody" refers to a specific type of bispecific antibody with two distinct heavy chains that can each form with the same light chain to bind to two structurally distinct targets.

"Fragment-based" bispecific antibodies or bispecific antibodies comprising a "single chain variable fragment" or "scFv" of this disclosure can refer to a single chain antibody, or fragment thereof, that comprises two binding moieties and a linker connecting the two binding moieties. The linker may be a polypeptide linker or other linker of suitable flexibility so as not to inhibit binding of either targeting moiety. Fragment based bispecific antibody formats include tandem $V_{HH}$ antibodies, tandem scFvs, scFv-Fabs, $F(ab)_2$, dual-affinity retargeting antibodies (DARTs). Such fragment-based antibodies can be further manipulated to comprise additional binding moieties with specificity for a given target e.g., $A_2$:$B_1$, $A_1$:$B_2$ or $A_2$:$B_2$, or with fragments of an Fc region to improve pharmacokinetics or promote ADCC, ADCP, or CDC.

A "binding moiety" refers to a portion of a molecule, peptide, polypeptide, antibody, or antibody fragment that mediates specific binding to a recited target or antigen or epitope. By way of example, the binding moiety of an antibody may comprise a heavy-chain/light-chain variable region pair or one or more complementarity determining regions (CDRs).

Specific binding or binding of antibody molecules described herein refers to binding mediated by one or more CDR portions of the antibody. Not all CDRs may be required for specific binding. Specific binding can be demonstrated for example by an ELISA against a specific recited target or antigen that shows significant increase in binding compared to an isotype control antibody.

A "target" as referred to herein refers to the portion of a molecule that participates with a binding moiety of a molecule, peptide, polypeptide, antibody, or antibody fragment. A target can comprise an amino acid sequence and/or a carbohydrate, lipid or other chemical entity. An "antigen" is a target comprising a portion that is able to be bound by an adaptive immune molecule such as an antibody or antibody fragment, B-cell receptor, or T-cell receptor.

An "epitope" as described herein refers to the one or more contact regions of an antibody. The contact region of an antibody consists of a discreet number of amino acids contacted by amino acid residues of the antibody (generally CDR residues) and adjacent residues contiguous with the contact residues. For example, the contact region may consist of a continuous stretch of a target protein that is between 5 to 20 amino acids, 5 to 15 amino acids, or 5 to 10 amino acids. An antibody or bispecific antibody may bind more than one contact region that are separated by 10, 20, 30, 40, 50, 75, or 100 amino acids or more as a result of protein folding or multi-specificity of a bispecific antibody. Epitopes may be determined using X-ray crystallography, hydrogen-deuterium exchange mass-spec, alanine spanning mutagenesis, competition with excess synthetic peptides as determined by immunoblot, ELISA, surface plasmon radiance, flow cytometry or any other suitable protein binding assay.

As referred to herein "competition" can be determined by incubating a target with a first antibody or bispecific antibody with excess of a test antibody and observing a decrease in binding of the first antibody. Such decrease in binding can be observed using immunoblot, ELISA, surface plasmon radiance, flow cytometry or any other suitable protein binding assay.

The "valency" of a bispecific or multi-specific molecule refers to the number of targets a recited molecule, peptide, polypeptide, antibody, or antibody fragment is able to bind. For instance, a molecule that is monovalent is able to bind to one molecule of a specific target, a bivalent molecule is able to bind to two molecules, and a tetravalent molecule is able to bind four targets.

A "humanized" antibody is an antibody in which all or substantially all CDR amino acid residues are derived from non-human CDRs and all or substantially all FR amino acid residues are derived from human FRs. A humanized antibody optionally can include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human. Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

"ADCC" or "antibody dependent cell-mediated cytotoxicity" as used herein, refers to the cell-mediated reaction wherein nonspecific cytotoxic cells that express FcγRs recognize bound antibody on a target cell and subsequently cause lysis of the target cell. ADCC can be correlated with binding to FcγRIIIa wherein increased binding to FcγRIIIa leads to an increase in ADCC activity. "ADCP" or antibody dependent cell-mediated phagocytosis, as used herein, can refer to the cell-mediated reaction wherein nonspecific cytotoxic cells that express FcγRs recognize bound antibody on a target cell and subsequently cause phagocytosis of the target cell.

The terms "polypeptide" and "protein" are used interchangeably and refers to a polymer of amino acid residues, and are not limited to a minimum length. Polypeptides, including the provided antibodies and antibody chains and other peptides, e.g., linkers and binding peptides, can include amino acid residues including natural and/or non-natural amino acid residues. The terms also include post-expression modifications of the polypeptide, for example, glycosylation, sialylation, acetylation, phosphorylation, and the like. In some aspects, the polypeptides can contain modifications with respect to a native or natural sequence, as long as the protein maintains the desired activity. These modifications can be deliberate, as through site-directed mutagenesis, or can be accidental, such as through mutations of hosts which produce the proteins or errors due to PCR amplification.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Amino acid sequence variants of the antibodies provided herein can be contemplated and conceived. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of known techniques. For example, it may be desirable to improve the binding affinity and/or other biological properties of the antibody amino acid sequence variants of an antibody can be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Antibody variants having one or more amino acid substitutions can be provided. Sites of interest for mutagenesis by substitution include the CDRs and FRs. Amino acid substitutions can be introduced into an antibody of interest and the products screened for a desired activity, e.g., retained/improved antigen binding, decreased immunogenicity, or improved ADCC or CDC.

The antibodies described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

As used herein, the terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87:2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215:403-410, 1990). Percent homology of sequences can be determined using the most recent version of BLAST, as of the filing date of this application.

The nucleic acids encoding the antibodies described herein can be used to infect, transfect, transform, or otherwise render a suitable cell transgenic for the nucleic acid, thus enabling the production of antibodies for commercial or therapeutic uses. Standard cell lines and methods for the production of antibodies from a large-scale cell culture are known in the art. See e.g., Li et al., "Cell culture processes for monoclonal antibody production." *Mabs.* 2010 September-October; 2(5): 466-477. In certain embodiments, the cell is a Eukaryotic cell. In certain embodiments, the Eukaryotic cell is a mammalian cell. In certain embodiments, the mammalian cell is a cell line useful for producing antibodies is a Chines Hamster Ovary cell (CHO) cell, an NS0 murine myeloma cell, or a PER.C6® cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

The section headings used herein are for organizational purposes only and are not to be construed as limiting the subject matter described.

EGFR Binding Antibodies

Described herein are antibodies that bind to and inhibit signaling through EGFR. Such antibodies are useful for the treatment for disorders that involve aberrant EGFR signaling. In some embodiments, the antibodies bind to EGFR domain II.

In certain embodiments, the EGFR antibodies and bispecific antibodies comprise Domain II binding moieties comprising CDR sequences of any one or more of antibodies 2a, 2b, or 2c described herein. In certain embodiments, the EGFR antibodies and bispecific antibodies comprise Domain III binding moieties comprising CDR sequences of any one or more of antibodies 3a, 3b, or 3c described herein.

In certain embodiments, described herein, is an EGFR domain II binding antibody comprising: a) a heavy chain complementarity determining region 1 (HCDR1) comprising an amino acid sequence set forth in SEQ ID NO: 17; b) a heavy chain complementarity determining region 2 (HCDR2) comprising an amino acid sequence set forth in SEQ ID NO: 18; c) a heavy chain complementarity determining region 3 (HCDR3) comprising an amino acid sequence set forth in any one of SEQ ID NOs: 23 to 38; d) a light chain complementarity determining region 1 (LCDR1) comprising an amino acid sequence set forth in any one of SEQ ID NOs: 4 or 5; e) a light chain complementarity determining region 2 (LCDR2) comprising an amino acid sequence set forth in SEQ ID NO: 6; and f) a light chain complementarity determining region 3 (LCDR3) comprising an amino acid sequence set forth in SEQ ID NO: 7.

In certain embodiments, the EGFR domain II binding antibody of the current disclosure comprises an immunoglobulin heavy chain and an immunoglobulin light chain, wherein the immunoglobulin heavy chain comprises an amino acid sequence at least about 90%, 91%, 92%, 93%, 94%, 95%, 96%, 97%, 98%, 99%, or 100% identical to that set forth in SEQ ID NO: 16 or 20; and wherein the immunoglobulin light chain comprises an amino acid sequence at least about 90%, 95%, 97%, 99%, or 100% identical to that set forth in SEQ ID NO: 2 or 3.

In certain embodiments, the EGFR domain II binding antibody of the current disclosure comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 16 or 20; and wherein the immunoglobulin light chain comprises an amino acid sequence at least about 90%, 95%, 97%, 99%, or 100% identical to that set forth in SEQ ID NO: 2 or 3.

In certain embodiments, the EGFR domain II binding antibody of the current disclosure comprises an immunoglobulin heavy chain and an immunoglobulin light chain, wherein the immunoglobulin heavy chain comprises an amino acid sequence at least about 90% identical to that set forth in SEQ ID NO: 16 or 20; and wherein the immunoglobulin light chain comprises an amino acid sequence at least about 90% identical to that set forth in SEQ ID NO: 2 or 3.

In certain embodiments, the EGFR domain II binding antibody of the current disclosure comprises an immunoglobulin heavy chain and an immunoglobulin light chain, wherein the immunoglobulin heavy chain comprises an amino acid sequence at least about 95% identical to that set forth in SEQ ID NO: 16 or 20; and wherein the immunoglobulin light chain comprises an amino acid sequence at least about 95% identical to that set forth in SEQ ID NO: 2 or 3.

In certain embodiments, the EGFR domain II binding antibody of the current disclosure comprises an immunoglobulin heavy chain and an immunoglobulin light chain, wherein the immunoglobulin heavy chain comprises an amino acid sequence at least about 97% identical to that set forth in SEQ ID NO: 16 or 20; and wherein the immunoglobulin light chain comprises an amino acid sequence at least about 97% identical to that set forth in SEQ ID NO: 2 or 3.

In certain embodiments, the EGFR domain II binding antibody of the current disclosure comprises an immunoglobulin heavy chain and an immunoglobulin light chain, wherein the immunoglobulin heavy chain comprises an amino acid sequence at least about 98% identical to that set forth in SEQ ID NO: 16 or 20; and wherein the immunoglobulin light chain comprises an amino acid sequence at least about 98% identical to that set forth in SEQ ID NO: 2 or 3.

In certain embodiments, the EGFR domain II binding antibody of the current disclosure comprises an immunoglobulin heavy chain and an immunoglobulin light chain, wherein the immunoglobulin heavy chain comprises an amino acid sequence at least about 99% identical to that set forth in SEQ ID NO: 16 or 20; and wherein the immunoglobulin light chain comprises an amino acid sequence at least about 99% identical to that set forth in SEQ ID NO: 2 or 3.

In certain embodiments, the EGFR domain II binding antibody of the current disclosure comprises an immunoglobulin heavy chain and an immunoglobulin light chain, wherein the immunoglobulin heavy chain comprises an amino acid sequence identical to that set forth in SEQ ID NO: 16 or 20; and wherein the immunoglobulin light chain comprises an amino acid sequence identical to that set forth in SEQ ID NO: 2 or 3.

In certain embodiments, the domain II binding antibody or antigen binding fragment thereof is chimeric or humanized. In certain embodiments, the domain II binding antibody or antigen binding fragment thereof is an IgG antibody. In certain embodiments, the domain II binding antibody or antigen binding fragment thereof is a Fab, $F(ab)_2$, a single-domain antibody, or a single chain variable fragment (scFv). In certain embodiments, the domain II binding antibody or antigen binding fragment thereof is a multispecific antibody. In certain embodiments, the domain II binding antibody or antigen binding fragment thereof is a bispecific antibody.

Described herein are antibodies that bind to and inhibit signaling through EGFR. Such antibodies are useful for the treatment for disorders that involve aberrant EGFR signaling. In some embodiments, the antibodies bind to EGFR domain III.

In certain embodiments, described herein, is an EGFR domain III binding antibody comprising: a) a heavy chain complementarity determining region 1 (HCDR1) comprising an amino acid sequence set forth in SEQ ID NO: 52; b) a heavy chain complementarity determining region 2 (HCDR2) comprising an amino acid sequence set forth in SEQ ID NO: 53; c) a heavy chain complementarity determining region 3 (HCDR3) comprising an amino acid sequence set forth in any one of SEQ ID NOs: 54 to 60; d) a light chain complementarity determining region 1 (LCDR1) comprising an amino acid sequence set forth in any one of SEQ ID NOs: 4 or 5; e) a light chain complementarity determining region 2 (LCDR2) comprising an amino acid sequence set forth in SEQ ID NO: 6; and f) a light chain complementarity determining region 3 (LCDR3) comprising an amino acid sequence set forth in SEQ ID NO: 7.

In certain embodiments, the EGFR domain III binding antibody of the current disclosure comprises an immunoglobulin heavy chain and an immunoglobulin light chain, wherein the immunoglobulin heavy chain comprises an amino acid sequence at least about 90%, 91%, 92%, 93%, 94%, 95%, 96%, 97%, 98%, 99%, or 100% identical to that set forth in SEQ ID NO: 51; and wherein the immunoglobulin light chain comprises an amino acid sequence at least about 90%, 91%, 92%, 93%, 94%, 95%, 96%, 97%, 98%, 99%, or 100% identical to that set forth in SEQ ID NO: 2 or 3.

In certain embodiments, the EGFR domain III binding antibody of the current disclosure comprises an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 51; and wherein the immunoglobulin light chain comprises an amino acid sequence at least about 90%, 95%, 97%, 99%, or 100% identical to that set forth in SEQ ID NO: 2 or 3.

In certain embodiments, the EGFR domain III binding antibody of the current disclosure comprises an immunoglobulin heavy chain and an immunoglobulin light chain, wherein the immunoglobulin heavy chain comprises an amino acid sequence at least about 90% identical to that set forth in SEQ ID NO: 51; and wherein the immunoglobulin light chain comprises an amino acid sequence at least about 90% identical to that set forth in SEQ ID NO: 2 or 3.

In certain embodiments, the EGFR domain III binding antibody of the current disclosure comprises an immunoglobulin heavy chain and an immunoglobulin light chain, wherein the immunoglobulin heavy chain comprises an amino acid sequence at least about 95% identical to that set forth in SEQ ID NO: 51; and wherein the immunoglobulin light chain comprises an amino acid sequence at least about 95% identical to that set forth in SEQ ID NO: 2 or 3.

In certain embodiments, the EGFR domain III binding antibody of the current disclosure comprises an immunoglobulin heavy chain and an immunoglobulin light chain, wherein the immunoglobulin heavy chain comprises an amino acid sequence at least about 97% identical to that set forth in SEQ ID NO: 51; and wherein the immunoglobulin light chain comprises an amino acid sequence at least about 97% identical to that set forth in SEQ ID NO: 2 or 3.

In certain embodiments, the EGFR domain III binding antibody of the current disclosure comprises an immunoglobulin heavy chain and an immunoglobulin light chain, wherein the immunoglobulin heavy chain comprises an amino acid sequence at least about 98% identical to that set forth in SEQ ID NO: 51; and wherein the immunoglobulin light chain comprises an amino acid sequence at least about 98% identical to that set forth in SEQ ID NO: 2 or 3.

In certain embodiments, the EGFR domain III binding antibody of the current disclosure comprises an immunoglobulin heavy chain and an immunoglobulin light chain, wherein the immunoglobulin heavy chain comprises an amino acid sequence at least about 99% identical to that set forth in SEQ ID NO: 51; and wherein the immunoglobulin light chain comprises an amino acid sequence at least about 99% identical to that set forth in SEQ ID NO: 2 or 3.

In certain embodiments, the EGFR domain III binding antibody of the current disclosure comprises an immunoglobulin heavy chain and an immunoglobulin light chain, wherein the immunoglobulin heavy chain comprises an amino acid sequence identical to that set forth in SEQ ID NO: 51; and wherein the immunoglobulin light chain comprises an amino acid sequence identical to that set forth in SEQ ID NO: 2 or 3.

In certain embodiments, the domain III binding antibody or antigen binding fragment thereof is chimeric or humanized. In certain embodiments, the domain III binding antibody or antigen binding fragment thereof is an IgG antibody. In certain embodiments, the domain III binding antibody or antigen binding fragment thereof is a Fab, $F(ab)_2$, a single-domain antibody, or a single chain variable fragment (scFv). In certain embodiments, the domain III binding antibody or antigen binding fragment thereof is a multispecific antibody. In certain embodiments, the domain III binding antibody or antigen binding fragment thereof is a bispecific antibody.

EGFR Binding Bispecific Molecules

Provided herein are bispecific or multivalent antibody molecules comprising a first binding component configured to bind a first target and a second binding component configured to bind a second target, wherein the first target comprises an EGFR epitope, and wherein the second target comprises a distinct EGFR epitope. In certain embodiments, one binding moiety of the bispecific antibody binds to domain II of EGFR and the other binding moiety binds to domain III of EGFR. In certain embodiments, one binding moiety of the bispecific antibody binds to domain II of human EGFR and the other binding moiety binds to domain III of human EGFR. The bispecific molecule may be selective for the "open configuration" of EGFR (including human EGFR), distinguishing them from antibodies that bind the closed form such as Cetuximab or Panitumumab. Such bispecific antibodies are advantageous as they can inhibit EGFR activity in the presence of ligand or in the absence of ligand when EGFR can open due to a mass action effect as a result of high-expression levels.

A multispecific or bispecific antibody possesses the ability to specifically bind to at least two structurally distinct targets. The specific binding may be the result of two distinct binding moieties that are structurally distinct at the molecular level, including but not limited to distinct non-identical amino acid sequences; or a single binding moiety that is able to specifically bind to two structurally distinct targets. A molecule, peptide, polypeptide, antibody, or antibody fragment referred to as "multi-specific" or "multivalent" or "bispecific" can refer to a molecule that possesses the ability to specifically bind to at least two structurally distinct targets. In some embodiments, the first or the second binding component of the bispecific antibody comprises a polypeptide. In certain embodiments, the first or the second binding component consists of a polypeptide. In some embodiments, the first and the second binding component of the bispecific antibody comprises a polypeptide. In certain embodiments, the first and the second binding component consist of a polypeptide. In certain embodiments, the polypeptide of the first or second binding component comprises an amino acid sequence at least 100 amino acid residues in length. In certain embodiments, the polypeptide of the first and second binding component comprise an amino acid sequence at least 100 amino acid residues in length.

A bispecific molecule can be a bispecific antibody that preserves at least one fragment of an antibody able to specifically bind with a target, for example, a variable region, heavy or light chain, or one or more complementarity determining regions from an antibody molecule. In some embodiments, the antibody described herein is a bispecific antibody and/or dual antigen-binding fragment thereof. Bispecific antibodies possess the ability to bind to two structurally distinct targets or antigens. In some embodiments, the bispecific antibody comprises a first binding component configured to bind a first target and a second binding component configured to bind a second target, wherein the first target comprises EGFR domain II, and wherein the second target comprises an EGFR domain III.

The bispecific antibodies described herein reduce or eliminate signaling through EGFR. In certain embodiments, the bispecific antibodies inhibit signaling through the EGFR open confirmation. In certain embodiments, the binding affinity of the bispecific antibody when measured as $K_D$ is about 500 nanomolar or less, about 100 nanomolar or less, about 50 nanomolar or less, about 30 nanomolar or less, about 20 nanomolar or less, about 10 nanomolar or less.

Described herein, in certain embodiments, is a bispecific antibody or antigen binding fragment thereof comprising an EGFR domain II and an EGFR domain III binding moiety, wherein the EGFR domain II binding moiety comprises: a) a heavy chain complementarity determining region 1 (HCDR1) comprising an amino acid sequence set forth in any one of SEQ ID NOs: 17; b) a heavy chain complementarity determining region 2 (HCDR2) comprising an amino acid sequence set forth in any one of SEQ ID NOs: 18; c) a heavy chain complementarity determining region 3 (HCDR3) comprising an amino acid sequence set forth in any one of SEQ ID NOs: 23 to 38; d) a light chain complementarity determining region 1 (LCDR1) comprising an amino acid sequence set forth in any one of SEQ ID NOs: 4 or 5; e) a light chain complementarity determining region 2 (LCDR2) comprising an amino acid sequence set forth in any one of SEQ ID NOs: 6; and/or f) a light chain complementarity determining region 3 (LCDR3) comprising an amino acid sequence set forth in any one of SEQ ID NOs: 7; and wherein the EGFR domain III antigen binding moiety comprises: g) a heavy chain complementarity determining region 1 (HCDR1) comprising an amino acid sequence set forth in any one of SEQ ID NOs: 52; h) a heavy chain complementarity determining region 2 (HCDR2) comprising an amino acid sequence set forth in any one of SEQ ID NOs: 53; i) a heavy chain complementarity determining region 3 (HCDR3) comprising an amino acid sequence set forth in any one of SEQ ID NOs: 54 to 60; j) a light chain complementarity determining region 1 (LCDR1) comprising an amino acid sequence set forth in any one of SEQ ID NOs: 4 or 5; k) a light chain complementarity determining region 2 (LCDR2) comprising an amino acid sequence set forth in any one of SEQ ID NOs: 6; and 1) a light chain complementarity determining region 3 (LCDR3) comprising an amino acid sequence set forth in any one of SEQ ID NOs: 7. In certain embodiments, the bispecific antibody or antigen binding fragment thereof is chimeric or humanized. In certain embodiments, the bispecific antibody or antigen binding fragment thereof comprises an IgG constant region.

In certain embodiments, the EGFR domain II binding moiety and the EGFR domain III binding moiety comprises a common immunoglobulin light chain, wherein the common immunoglobulin light chain comprises an amino acid sequence at least about 90%, 91%, 92%, 93%, 94%, 95%, 96%, 97%, 98%, 99%, or 100% identical to that set forth in SEQ ID NO: 2 or 3.

In certain embodiments, the EGFR domain II binding moiety and the EGFR domain III binding moiety comprises a common immunoglobulin light chain, wherein the common immunoglobulin light chain comprises an amino acid sequence at least about 90% identical to that set forth in SEQ ID NO: 2 or 3.

In certain embodiments, the EGFR domain II binding moiety and the EGFR domain III binding moiety comprises a common immunoglobulin light chain, wherein the common immunoglobulin light chain comprises an amino acid sequence at least about 95% identical to that set forth in SEQ ID NO: 2 or 3.

In certain embodiments, the EGFR domain II binding moiety and the EGFR domain III binding moiety comprises a common immunoglobulin light chain, wherein the common immunoglobulin light chain comprises an amino acid sequence at least about 97% identical to that set forth in SEQ ID NO: 2 or 3.

In certain embodiments, the EGFR domain II binding moiety and the EGFR domain III binding moiety comprises a common immunoglobulin light chain, wherein the common immunoglobulin light chain comprises an amino acid sequence at least about 99% identical to that set forth in SEQ ID NO: 2 or 3.

In certain embodiments, the EGFR domain II binding moiety and the EGFR domain III binding moiety comprises a common immunoglobulin light chain, wherein the common immunoglobulin light chain comprises an amino acid sequence identical to that set forth in SEQ ID NO: 2 or 3.

In certain embodiments, the EGFR domain II binding moiety comprises an EGFR domain II binding immunoglobulin heavy chain, wherein the EGFR domain II binding immunoglobulin heavy chain comprises an amino acid sequence at least about 90%, 91%, 92%, 93%, 94%, 95%, 96%, 97%, 98%, 99%, or 100% identical to that set forth in SEQ ID NO: 16 or 20.

In certain embodiments, the EGFR domain II binding moiety comprises an EGFR domain II binding immunoglobulin heavy chain, wherein the EGFR domain II binding immunoglobulin heavy chain comprises an amino acid sequence at least about 90% identical to that set forth in SEQ ID NO: 16 or 20.

In certain embodiments, the EGFR domain II binding moiety comprises an EGFR domain II binding immunoglobulin heavy chain, wherein the EGFR domain II binding immunoglobulin heavy chain comprises an amino acid sequence at least about 95% identical to that set forth in SEQ ID NO: 16 or 20.

In certain embodiments, the EGFR domain II binding moiety comprises an EGFR domain II binding immunoglobulin heavy chain, wherein the EGFR domain II binding immunoglobulin heavy chain comprises an amino acid sequence at least about 97% identical to that set forth in SEQ ID NO: 16 or 20.

In certain embodiments, the EGFR domain II binding moiety comprises an EGFR domain II binding immunoglobulin heavy chain, wherein the EGFR domain II binding immunoglobulin heavy chain comprises an amino acid sequence at least about 98% identical to that set forth in SEQ ID NO: 16 or 20.

In certain embodiments, the EGFR domain II binding moiety comprises an EGFR domain II binding immunoglobulin heavy chain, wherein the EGFR domain II binding immunoglobulin heavy chain comprises an amino acid sequence at least about 99% identical to that set forth in SEQ ID NO: 16 or 20.

In certain embodiments, the EGFR domain II binding moiety comprises an EGFR domain II binding immunoglobulin heavy chain, wherein the EGFR domain II binding immunoglobulin heavy chain comprises an amino acid sequence identical to that set forth in SEQ ID NO: 16 or 20.

In certain embodiments, the EGFR domain III binding moiety comprises an EGFR domain III binding immunoglobulin heavy chain, wherein the EGFR domain III binding immunoglobulin heavy chain comprises an amino acid sequence at least about 90%, 91%, 92%, 93%, 94%, 95%, 96%, 97%, 98%, 99%, or 100% identical to that set forth in SEQ ID NO: 51.

In certain embodiments, the EGFR domain III binding moiety comprises an EGFR domain III binding immunoglobulin heavy chain, wherein the EGFR domain III binding immunoglobulin heavy chain comprises an amino acid sequence at least about 90% identical to that set forth in SEQ ID NO: 51.

In certain embodiments, the EGFR domain III binding moiety comprises an EGFR domain III binding immunoglobulin heavy chain, wherein the EGFR domain III binding immunoglobulin heavy chain comprises an amino acid sequence at least about 95% identical to that set forth in SEQ ID NO: 51.

In certain embodiments, the EGFR domain III binding moiety comprises an EGFR domain III binding immunoglobulin heavy chain, wherein the EGFR domain III binding immunoglobulin heavy chain comprises an amino acid sequence at least about 97% identical to that set forth in SEQ ID NO: 51.

In certain embodiments, the EGFR domain III binding moiety comprises an EGFR domain III binding immunoglobulin heavy chain, wherein the EGFR domain III binding immunoglobulin heavy chain comprises an amino acid sequence at least about 98% identical to that set forth in SEQ ID NO: 51.

In certain embodiments, the EGFR domain III binding moiety comprises an EGFR domain III binding immunoglobulin heavy chain, wherein the EGFR domain III binding immunoglobulin heavy chain comprises an amino acid sequence at least about 99% identical to that set forth in SEQ ID NO: 51.

In certain embodiments, the EGFR domain III binding moiety comprises an EGFR domain III binding immunoglobulin heavy chain, wherein the EGFR domain III binding immunoglobulin heavy chain comprises an amino acid sequence identical to that set forth in SEQ ID NO: 51.

Common Light Chain Bispecific IgG

Disclosed herein are bispecific antibodies having a common light chain bispecific IgG structure, as shown in FIG. 1. Bispecific antibodies with a single, identical common light chain allow for the light chain variable region to productively associate with either heavy chain variable region reducing unproductive antigen binding moiety formation that is seen when multiple distinct light chains are used. Such bispecific structures have significant benefits for the formation and assembly of bispecific antibodies during production by reducing undesired products. Generally, the structure of a common light chain comprises a first and a second IgG heavy chain. Each heavy chain comprises a VH, CH1, CH2, and CH3 domain. The common light chain bispecific IgG structure also comprises a light chain comprising a VL domain and a CL domain. Generally, the first heavy chain will comprise a sequence derived from the heavy chain of an antibody with a first specificity; and the second heavy chain will comprise a heavy chain from an antibody with a second specificity. The light chain that pairs with the first and the second heavy chain will be identical, and can be derived from the light chain of an antibody with either specificity, or a separate specificity. The common light chain bispecific IgG structure can comprise a first and a second heavy chain molecule that further comprises mutations within the CH3 domain that promote coupling of the first and the second heavy chain and/or prevent coupling of a first heavy chain to another first heavy chain or a second heavy chain to another second heavy chain. The mutations can physically (e.g. steric hinderance, “knobs” into “holes”) or biochemically (e.g. electrostatic interactions) prevent coupling of the two first heavy chain molecules or two second heavy chain molecules. Exemplary knob into hole mutations can comprise T366W (EU numbering) in one heavy chain and T366S/L368A/Y407V (EU numbering) in a second heavy chain. Exemplary mutations that facilitate coupling of a first and a second heavy chain molecule are disclosed, for example in WO2009089004, U.S. Pat. No. 8,642,745, US PG-PUB: US20140322756 and “The making of bispecific antibodies” MAbs. 2017 February-March; 9(2): 182-212. The common light chain bispecific IgG structure can also comprise carbohydrate molecules coupled thereto or additional modifications thereof.

In certain embodiments, the bispecific antibody or antigen binding fragment thereof comprises an EGFR domain II binding immunoglobulin heavy chain and the EGFR domain III binding immunoglobulin heavy chain, comprising an IgG constant region; the common immunoglobulin light chain is associated with the EGFR domain II binding immunoglobulin heavy chain and the EGFR domain III binding immunoglobulin heavy chain; and the EGFR domain II binding immunoglobulin heavy chain and the EGFR domain III binding immunoglobulin heavy chain associate with each other. In certain embodiments, the IgG constant region of the EGFR domain II binding immunoglobulin heavy chain and the EGFR domain III binding immunoglobulin heavy chain differ at one or more amino acid positions such that the heterodimerization of the EGFR domain II binding immunoglobulin heavy chain and the EGFR domain III binding immunoglobulin heavy chain is favored. In certain embodiments, the EGFR domain II binding immunoglobulin heavy chain and the EGFR domain III binding immunoglobulin heavy chain comprises a T366W substitution (EU numbering) and the other of the EGFR domain II binding immunoglobulin heavy chain or the EGFR domain III binding immunoglobulin heavy chain comprises a T366S/L368A/Y407V substitution (EU numbering), such that the heterodimerization of the EGFR domain II binding immunoglobulin heavy chain and the EGFR domain III binding immunoglobulin heavy chain is favored. In certain embodiments, the EGFR domain II binding immunoglobulin heavy chain and the EGFR domain III binding immunoglobulin heavy chain comprises one or more substitutions selected from Q347M, Y348F, T350D, T389W, L368M (EU numbering) and the other of the EGFR domain II binding immunoglobulin heavy chain or the EGFR domain III binding immunoglobulin heavy chain comprises one or more substitutions selected from S354I, E357L, K359S, T366S, L368A, and Y412V (EU numbering), such that the heterodimerization of the EGFR domain II binding immunoglobulin heavy chain and the EGFR domain III binding immunoglobulin heavy chain is favored. In certain embodiments, the EGFR domain II binding immunoglobulin heavy chain and the EGFR domain III binding immunoglobulin heavy chain comprises an amino acid sequence at least about 90%, 95%, 97%, 98%, 99% or is 100% identical to SEQ ID NO: 61 and the other of the EGFR domain II binding immunoglobulin heavy chain or the EGFR domain III binding immunoglobulin heavy chain comprises an amino acid sequence at least about 90%, 95%, 97%, 98%, 99% or is 100% identical to SEQ ID NO: 62, such that the heterodimerization of the EGFR domain II binding immunoglobulin heavy chain and the EGFR domain III binding immunoglobulin heavy chain is favored. In certain embodiments this sequence identity is maintained while preserving variant amino acids introduced to promote adequate homodimerization.

Pharmaceutically Acceptable Excipients, Carriers, And Diluents

Compositions comprising the antibodies of the current disclosure are included in a pharmaceutical composition comprising one or more pharmaceutically acceptable excipients, carriers, and diluents. In certain embodiments, the antibodies of the current disclosure are administered suspended in a sterile and/or isotonic solution. In certain embodiments, the solution comprises about 0.9% NaCl. In certain embodiments, the solution comprises about 5.0% dextrose. In certain embodiments, the solution further comprises one or more of: buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA.

Subcutaneous formulations for administration of antibodies can comprise one or more of: buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA. Additionally, a compound or molecule that relieves pain at the injection site can be included, such as hyaluronidase, for example at a concentration of from about 2,000 U/ml to about 12,000 U/ml.

In certain embodiments, the antibodies or bispecific antibodies of the current disclosure are shipped/stored lyophilized and reconstituted before administration. In certain embodiments, lyophilized antibody formulations comprise a bulking agent such as, mannitol, sorbitol, sucrose, trehalose, dextran 40, or combinations thereof. The lyophilized formulation can be contained in a vial comprised of glass or other suitable non-reactive material. The antibodies when formulated, whether reconstituted or not, can be buffered at a certain pH, generally less than about 7.5. In certain embodiments, the pH can be between 4.5 and 7.5, 4.5 and 7.0, 4.5 and 6.5, 4.5 and 6.0, or 5.5 or 5.0.

Also described herein are kits comprising one or more of the antibody molecules described herein in a suitable container and one or more additional components selected from: instructions for use; a diluent, an excipient, a carrier, and a device for administration.

In certain embodiments, described herein is a method of preparing a cancer treatment comprising admixing one or more pharmaceutically acceptable excipients, carriers, or diluents and an antibody molecule of the current disclosure. In certain embodiments, described herein is a method of preparing a cancer treatment for storage or shipping comprising lyophilizing one or more antibodies of the current disclosure.

Production and Manufacture

The nucleic acids encoding the antibodies or bispecific antibodies described herein can be used to infect, transfect, transform, or otherwise render a suitable cell transgenic for the nucleic acid, thus enabling the production of antibodies or bispecific antibodies for commercial or therapeutic uses. Standard cell lines and methods for the production of antibodies from a large-scale cell culture are known in the art. See e.g., Li et al., "Cell culture processes for monoclonal antibody production." Mabs. 2010 September-October; 2(5): 466-477.

In certain embodiments, a nucleic acid sequence encodes the antibodies or bispecific antibodies disclosed herein. In certain embodiments, the polynucleotide sequence encoding the antibodies or bispecific antibodies is operatively coupled to a eukaryotic regulatory sequence. In some embodiments, a cell comprises the nucleic acid sequence.

In some embodiments, a cell comprises a nucleic acid encoding the antibodies or bispecific antibodies disclosed herein. In certain embodiments, the cell comprises a prokaryotic cell. In certain embodiments, the prokaryotic cell is an *Escherichia coli* cell. In certain embodiments, the cell comprises a eukaryotic cell. In certain embodiments, the eukaryotic cell is a Chines Hamster Ovary (CHO) cell, an NS0 murine myeloma cell, or a human PER.C6 cell.

In certain embodiments, described herein is a method of making antibodies or bispecific antibodies comprising culturing a cell comprising a nucleic acid encoding a antibodies or bispecific antibodies under conditions in vitro sufficient to allow production and secretion of the antibodies or bispecific antibodies.

In certain embodiments, described herein, is a master cell bank comprising: (a) a mammalian cell line comprising a nucleic acid encoding an antibody described herein integrated at a genomic location; and (b) a cryoprotectant. In certain embodiments, the cryoprotectant comprises glycerol. In certain embodiments, the master cell bank comprises: (a) a CHO cell line comprising a nucleic acid encoding the antibodies or bispecific antibodies integrated at a genomic location; and (b) a cryoprotectant. In certain embodiments, the cryoprotectant comprises glycerol or DMSO or both. In certain embodiments, the master cell bank is contained in a suitable vial or container able to withstand freezing by liquid nitrogen.

Also described herein are methods of making antibodies or bispecific antibodies described herein. Such methods comprise incubating a cell or cell-line comprising a nucleic acid encoding the antibodies or bispecific antibodies in a cell culture medium under conditions sufficient to allow for expression and secretion of the antibodies or bispecific antibodies, and further harvesting the antibodies or bispecific antibodies from the cell culture medium. The harvesting can further comprise one or more purification steps to remove live cells, cellular debris, non-antibody proteins or polypeptides, undesired salts, buffers, and medium components. In certain embodiments, the additional purification step(s) include centrifugation, ultracentrifugation, protein A, protein G, protein A/G, or protein L purification, and/or ion exchange chromatography.

Methods of Use

In certain embodiments, disclosed herein, are bispecific antibodies useful for the treatment of a cancer or tumor. Treatment refers to a method that seeks to improve or ameliorate the condition being treated. With respect to cancer, treatment includes, but is not limited to, reduction of tumor volume, reduction in growth of tumor volume, increase in progression-free survival, or overall life expectancy. In certain embodiments, treatment will affect remission of a cancer being treated. In certain embodiments, treatment encompasses use as a prophylactic or maintenance dose intended to prevent reoccurrence or progression of a previously treated cancer or tumor. It is understood by those of skill in the art that not all individuals will respond equally or at all to a treatment that is administered, nevertheless these individuals are considered to be treated.

In certain embodiments, the cancer or tumor is a solid tissue cancer or tumor. In certain embodiments, the cancer or tumor is a blood cancer. In certain embodiments, the cancer is metastatic. In certain embodiments, the cancer is one associated with aberrant EGFR expression, such as over expression. In certain embodiments, the cancer or tumor is colorectal cancer. In certain embodiments, the cancer or tumor is metastatic colorectal cancer. In certain embodiments, the cancer or tumor is head and neck cancer. In certain embodiments, the cancer or tumor is metastatic head and neck cancer. In certain embodiments, the cancer or tumor comprises non-small cell lung cancer (NSCLC).

In certain embodiments, the antibodies and bispecific antibodies described can be administered to a subject in need thereof by any route suitable for the administration of antibody-containing pharmaceutical compositions, such as, for example, subcutaneous, intraperitoneal, intravenous, intramuscular, intratumoral, or intracerebral, etc. In certain embodiments, the antibodies are administered intravenously. In certain embodiments, the antibodies are administered subcutaneously. In certain embodiments, the antibodies are administered intratumoral. In certain embodiments, the antibodies are administered on a suitable dosage schedule, for example, weekly, twice weekly, monthly, twice monthly, once every two weeks, once every three weeks, or once a month etc. The antibodies can be administered in any therapeutically effective amount. In certain embodiments, the therapeutically acceptable amount is between about 0.1 mg/kg and about 50 mg/kg. In certain embodiments, the therapeutically acceptable amount is between about 1 mg/kg and about 40 mg/kg. In certain embodiments, the therapeutically acceptable amount is between about 5 mg/kg and about 30 mg/kg. Therapeutically effective amounts include amounts that are sufficient to ameliorate one or more symptoms associated with the disease or affliction to be treated.

Specific Embodiments

1. Described herein in one embodiment is an antibody or antigen binding fragment thereof comprising: (a) a heavy chain complementarity determining region 1 (HCDR1) comprising an amino acid sequence set forth in SEQ ID NO: 17; (b) a heavy chain complementarity determining region 2 (HCDR2) comprising an amino acid sequence set forth in SEQ ID NO: 18; (c) a heavy chain complementarity determining region 3 (HCDR3) comprising an amino acid sequence set forth in any one of SEQ ID NOs: 23 to 38; (d) a light chain complementarity determining region 1 (LCDR1) comprising an amino acid sequence set forth in any one of SEQ ID NOs: 4 or 5; (e) a light chain complementarity determining region 2 (LCDR2) comprising an amino acid sequence set forth in SEQ ID NO: 6; and/or (f) a light chain complementarity determining region 3 (LCDR3) comprising an amino acid sequence set forth in SEQ ID NO: 7; wherein the antibody binds to EGFR domain II.

2. The antibody or antigen binding fragment thereof of embodiment 1, wherein the antibody or antigen binding fragment thereof is chimeric or humanized.
3. The antibody or antigen binding fragment thereof of embodiment 1 or 2, wherein the antibody or antigen binding fragment thereof is an IgG antibody.
4. The antibody or antigen binding fragment thereof of embodiment 1 or 2, wherein the antibody or antigen binding fragment thereof is a Fab, $F(ab)_2$, a single-domain antibody, or a single chain variable fragment (scFv).
5. The antibody or antigen binding fragment thereof of any one of embodiments 1 to 4, wherein the antibody or antigen binding fragment thereof is a multispecific antibody.
6. The antibody or antigen binding fragment thereof of any one of embodiments 1 to 5, wherein the antibody or antigen binding fragment thereof is a bispecific antibody.
7. The antibody or antigen binding fragment thereof of any one of embodiments 1 to 6, comprising an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 16 or 20; and wherein the immunoglobulin light chain comprises an amino acid sequence at least about 90%, 95%, 97%, 99%, or 100% identical to that set forth in SEQ ID NO: 2 or 3.
8. The antibody or antigen binding fragment thereof of any one of embodiments 1 to 7, wherein the antibody or antigen binding fragment binds to EGFR with a $K_D$ of 50 nanomolar or less.
9. The antibody or antigen binding fragment thereof of any one of embodiments 1 to 7, wherein the antibody or antigen binding fragment binds to EGFR with a $K_D$ of 10 nanomolar or less.
10. An antibody or antigen binding fragment comprising: (a) a heavy chain complementarity determining region 1 (HCDR1) comprising an amino acid sequence set forth in SEQ ID NO: 52; (b) a heavy chain complementarity determining region 2 (HCDR2) comprising an amino acid sequence set forth in SEQ ID NO: 53; (c) a heavy chain complementarity determining region 3 (HCDR3) comprising an amino acid sequence set forth in any one of SEQ ID NOs: 54 to 60; (d) a light chain complementarity determining region 1 (LCDR1) comprising an amino acid sequence set forth in any one of SEQ ID NOs: 4 or 5; (e) a light chain complementarity determining region 2 (LCDR2) comprising an amino acid sequence set forth in SEQ ID NO: 6; and/or (f) a light chain complementarity determining region 3 (LCDR3) comprising an amino acid sequence set forth in SEQ ID NO: 7; wherein the antibody binds to EGFR domain III.
11. The antibody or antigen binding fragment thereof of embodiment 10, wherein the antibody or antigen binding fragment thereof is chimeric or humanized.
12. The antibody or antigen binding fragment thereof of embodiment 10 or 11, wherein the antibody or antigen binding fragment thereof is an IgG antibody.
13. The antibody or antigen binding fragment thereof of embodiment 10 or 11, wherein the antibody or antigen binding fragment thereof is a Fab, $F(ab)_2$, a single-domain antibody, or a single chain variable fragment (scFv).
14. The antibody or antigen binding fragment thereof of any one of embodiments 10 to 13, wherein the antibody or antigen binding fragment thereof is a multispecific antibody.
15. The antibody or antigen binding fragment thereof of any one of embodiments 10 to 14, wherein the antibody or antigen binding fragment thereof is a bispecific antibody.
16. The antibody or antigen binding fragment thereof of any one of embodiments 10 to 15, comprising an immunoglobulin heavy chain and an immunoglobulin light chain, wherein the immunoglobulin heavy chain comprises an amino acid sequence at least about 90%, 95%, 97%, 99%, or 100% identical to that set forth in SEQ ID NO: 51; and wherein the immunoglobulin light chain comprises an amino acid sequence at least about 90%, 95%, 97%, 99%, or 100% identical to that set forth in SEQ ID NO: 2 or 3.
17. The antibody or antigen binding fragment thereof of any one of embodiments 10 to 16, wherein the antibody or antigen binding fragment binds to EGFR with a $K_D$ of 500 nanomolar or less.
18. The antibody or antigen binding fragment thereof of any one of embodiments 10 to 16, wherein the antibody or antigen binding fragment binds to EGFR with a $K_D$ of 300 nanomolar or less.
19. An antibody or antigen binding fragment thereof of that binds the same epitope or overlaps in binding with the bispecific antibody or antigen binding fragment thereof of any one of embodiments 1 to 18.
20. An antibody or antigen binding fragment thereof of that competes for binding with the antibody or antigen binding fragment thereof of any one of embodiments 1 to 18.
21. A composition comprising the antibody or antigen binding fragment thereof of any one of embodiments 1 to 20 and a pharmaceutically acceptable diluent, carrier, or excipient.
22. A nucleic acid or plurality of nucleic acids comprising a polynucleotide sequence encoding the antibody, bispecific antibody or antigen binding fragment thereof of any one of embodiments 1 to 20.
23. A cell comprising the nucleic acid or plurality of nucleic acids of embodiment 22.
24. The cell of embodiment 23, wherein the cell is a eukaryotic cell.
25. The cell of embodiment 24, wherein the eukaryotic cell is a mammalian cell.
26. The cell of embodiment 23, wherein the cell is a prokaryotic cell.

27. Use of the antibody or antigen binding fragment thereof of any one of embodiments 1 to 20 in a method of treating cancer or tumor in an individual.

28. The use of embodiment 27, wherein the cancer or tumor is a solid tissue cancer or tumor.

29. The use of embodiment 27, wherein the cancer or tumor express EGFR

30. The use of embodiment 27, wherein the cancer or tumor over expresses EGFR.

31. The use of any one of embodiments 27 to 30, wherein the cancer or tumor comprises colorectal cancer.

32. The use of any one of embodiments 27 to 30, wherein the cancer or tumor comprises head and neck cancer.

33. A method of treating an individual afflicted with a cancer or a tumor comprising administering to the individual afflicted with the cancer or the tumor the antibody, bispecific antibody or antigen binding fragment thereof of any one of embodiments 1 to 20, thereby treating the cancer or the tumor.

34. The method of embodiment 33, wherein the cancer or the tumor expresses EGFR.

35. The method of embodiment 33, wherein the cancer overexpresses EGFR.

36. The method of embodiment 33, wherein the cancer or the tumor is a solid tissue cancer.

37. The method of any one of embodiments 33 to 36, wherein the cancer or tumor comprises colorectal cancer.

38. The method of any one of embodiments 33 to 36, wherein the cancer or tumor comprises head and neck cancer.

EXAMPLES

The following examples are included for illustrative purposes only and are not intended to limit the scope of the invention.

To facilitate the production of Abs that could be efficiently developed as potential therapeutics, a phage-displayed library of antigen-binding fragments (Fabs) using the framework of anti-ErbB2 therapeutic Ab Trastuzumab was constructed. The light chain sequence of the library was fixed as that of a Trastuzumab variant and the three heavy chain complementarity-determining regions (CDRs) were diversified (FIG. 2).

Following multiple rounds of selection for binding to the EGFR ectodomain (ECD), a number of antibodies capable of binding to EGFR as phage-Fab containing the LC variant were isolated and as IgGs produced with the wild-type Trastuzumab kappa light chain.

Figure 3A:
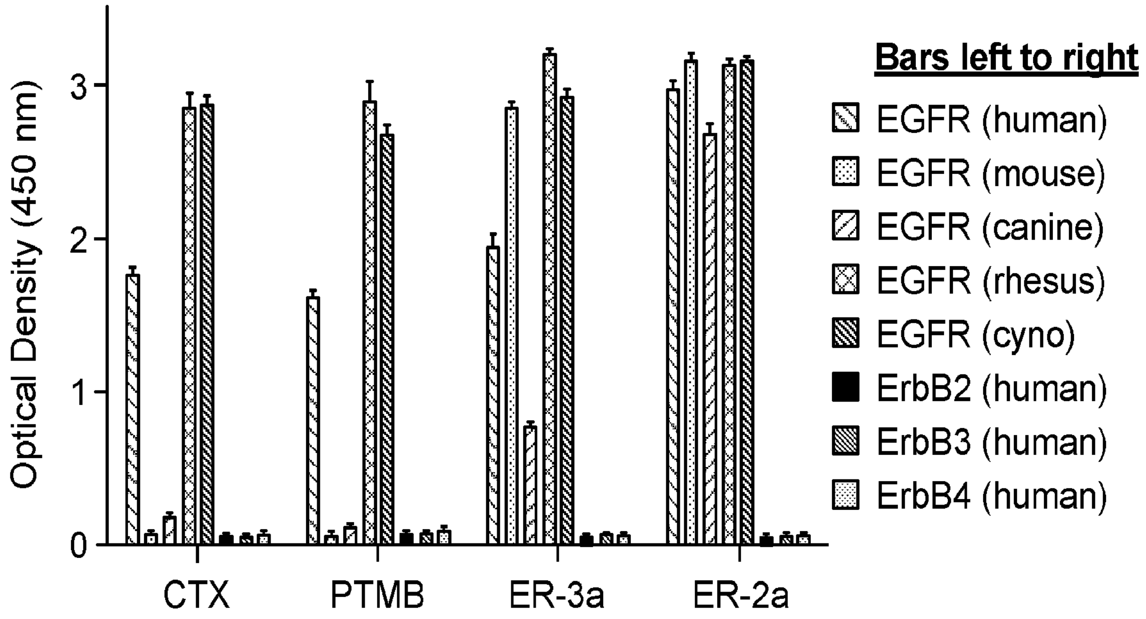
FIG. 3A illustrates specificity of clones 2a, 3a, Cetuximab (CTX) and Panitumumab (PTMB) for different EGFR families and EGFR from different species.

For characterization, focus was directed to two distinct anti-EGFR antibodies-named ER-2 and ER-3 which bound or did not bind to EGFR in the presence of EGF, respectively. Surface plasmon resonance (SPR) assays with purified IgG proteins revealed that ER-2 and ER-3 bound to EGFR with moderate affinities ($K_D$)=20 or 14 nM, respectively, (FIG. 2). To improve the affinities of Fabs ER-2 and ER-3, focused phage-displayed libraries that diversified the sequence of each heavy chain in a controlled and limited manner were diversified. Following selection and ELISA screening for binding to EGFR, a range of variants were diversified including the lead optimized variants of ER-2 and ER-3, which were named ER-2a and ER3a, respectively. SPR assays showed that IgGs ER-2a and ER3a bound to EGFR with affinities in the sub-nanomolar range ($K_D$)=0.28 or 0.33 nM, respectively) (FIG. 2). The specificities of Fabs ER-2a and ER-3a were assessed by ELISA (FIG. 3A). Both Fabs exhibited high selectivity across the human ErbB family, as strong binding was detected for EGFR but no binding was detected for ErbB2, ErbB3 or ErbB4. Moreover, both Fabs exhibited strong binding to mouse and rhesus and cynomologous monkey EGFR, and Fabs ER-2a and ER-3a bound strongly or weakly to canine EGFR, respectively. In contrast, Cetuximab (CTX) and Panitumumab (PTMB) bound to human and non-human primate EGFRs but not to mouse or canine EGFR.

Figure 3B:
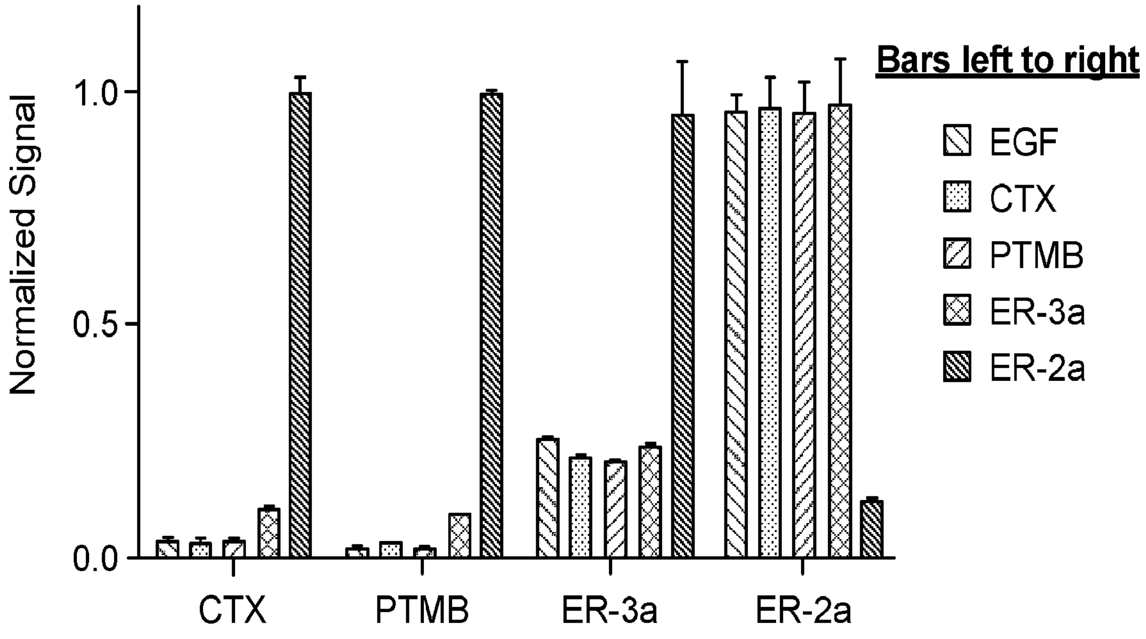
FIG. 3B illustrates competition assays using clones 2a, 3a, Cetuximab (CTX) and Panitumumab (PTMB).

ELISA was also used to determine whether saturating concentrations of EGF or various anti-EGFR IgGs could block binding of each Fab to immobilized EGFR (FIG. 3B). These assays confirmed that Fab ER-3a was blocked by its own IgG, EGF, CTX and PTMB, whereas in contrast, Fab ER-2a was blocked by its own IgG but not by any of the other ligands. Similarly, bio-layer interferometry (BLI) assays showed that binding of Fc-tagged EGF (EGF-Fc) to immobilized EGFR was reduced by EGF-Fc itself, and was abrogated by CTX, PTMB and IgG ER-3a, but not by IgG ER-2a (FIG. 3B).

Figure 3C:
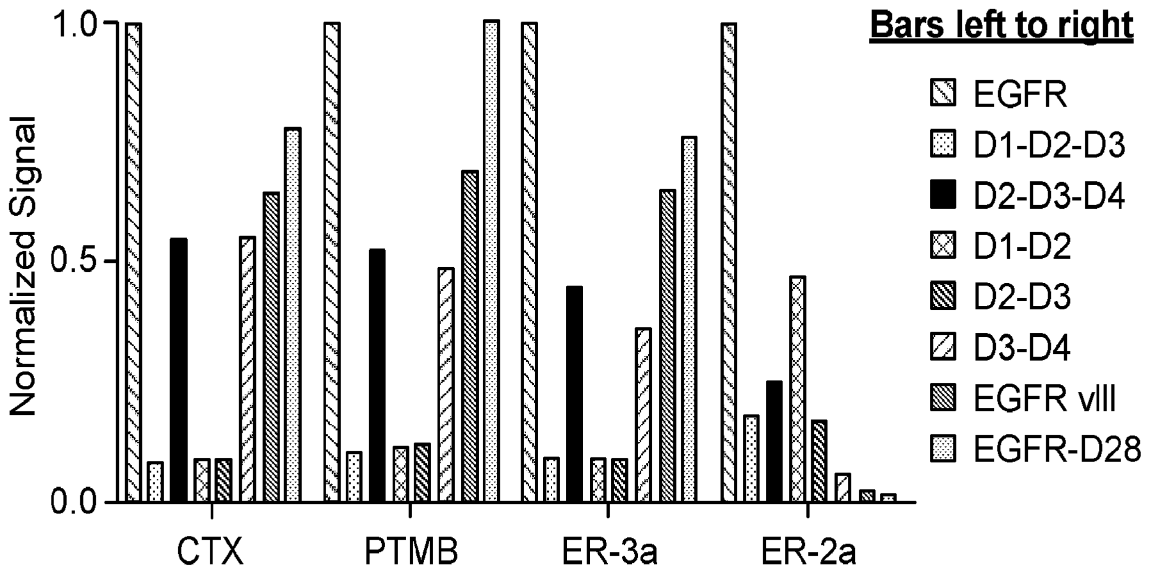
FIG. 3C illustrates EGFR domain binding for clones 2a, 3a, Cetuximab (CTX) and Panitumumab (PTMB).

To map epitopes, flow cytometry was used to assess the binding of IgGs to HEK293T cells transfected to express full-length EGFR or fragments of EGFR comprising double domains (D1-D2, D2-D3, D3-D4) or triple domains (D1-D2-D3, D2-D3-D4), and plotted binding signals at saturating IgG concentrations (FIG. 3C). Consistent with paratopes centered on domain III, CTX and PTMB bound to cells displaying EGFR fragments containing domain III (D3-D4 and D2-D3-D4), and IgG ER-3a exhibited the same binding pattern. In contrast, IgG ER-2a bound most strongly to cells displaying the D1-D2 fragment, also bound to cells displaying other fragments containing domain II (D2-D3, D1-D2-D3, D2-D3-D4), but did not bind to cells displaying a fragment lacking domain II (D3-D4). Moreover, CTX, PTMB and IgG ER-3a—but not IgG ER-2a—bound strongly to cells displaying EGFRvIII, which lacks all of domain I and most of domain II, and to cells displaying EGFR-D28, which lacks 28 residues (Cys240-Cys267) spanning the dimerization arm. Taken together, these results suggest that Ab ER-3a recognizes an epitope in domain III of EFGR, similar to the epitopes of CTX and PTMB, whereas Ab ER-2a recognize a distinct epitope centered on the dimerization arm within domain II.

Figure 3D:
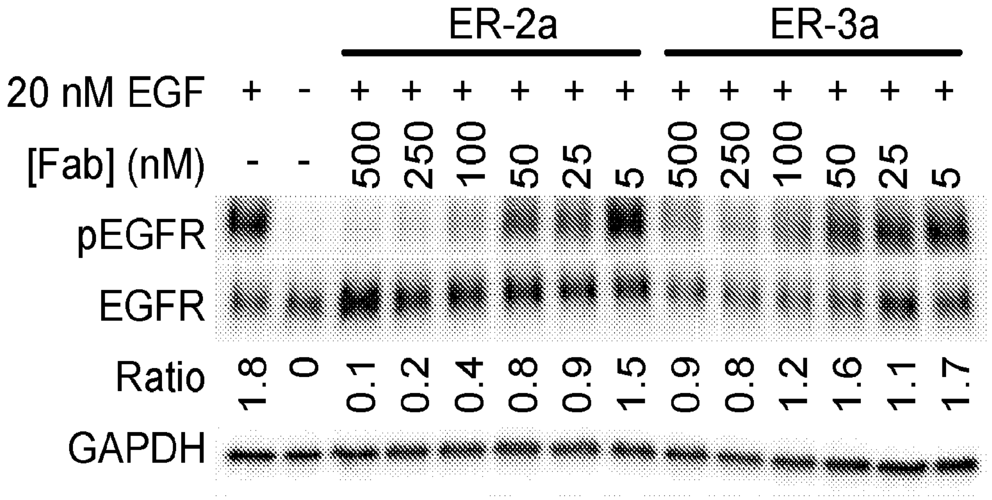

Finally, the effects of the Abs on the activation of EGFR by EGF in MDA-MB-468 breast cancer cells was investigated, which display high levels of endogenous EGFR. See Filmus J, Pollak M N, Cailleau R, & Buick R N (1985) MDA-468, a human breast cancer cell line with a high number of epidermal growth factor (EGF) receptors, has an amplified EGF receptor gene and is growth inhibited by EGF. *Biochem Biophys Res Commun* 128(2):898-905. Western blotting revealed that both Fabs reduced levels of phosphorylated EGFR in a dose-dependent manner, and Fab ER-2a was particularly potent in this assay (FIG. 3D).

To improve the biophysical properties of IgGs ER-2a and ER-3a, focused phage displayed libraries that diversified the sequence of each heavy chain in a controlled and limited manner were constructed, and following selection and ELISA screening for binding to EGFR, a range of variants were identified including the optimized variants of ER-2a and ER-3a, which we named ER-2b and ER-3b, respectively (FIG. 2). Finally, we screened the CDR H3 positions with Asp mutations to determine which amino acids would accommodate a charged negative side chain while still retaining binding to EGFR. Such Asp insertions would potentially improve the developability of a resulting clone by reducing aggregation.

Figure 4A:
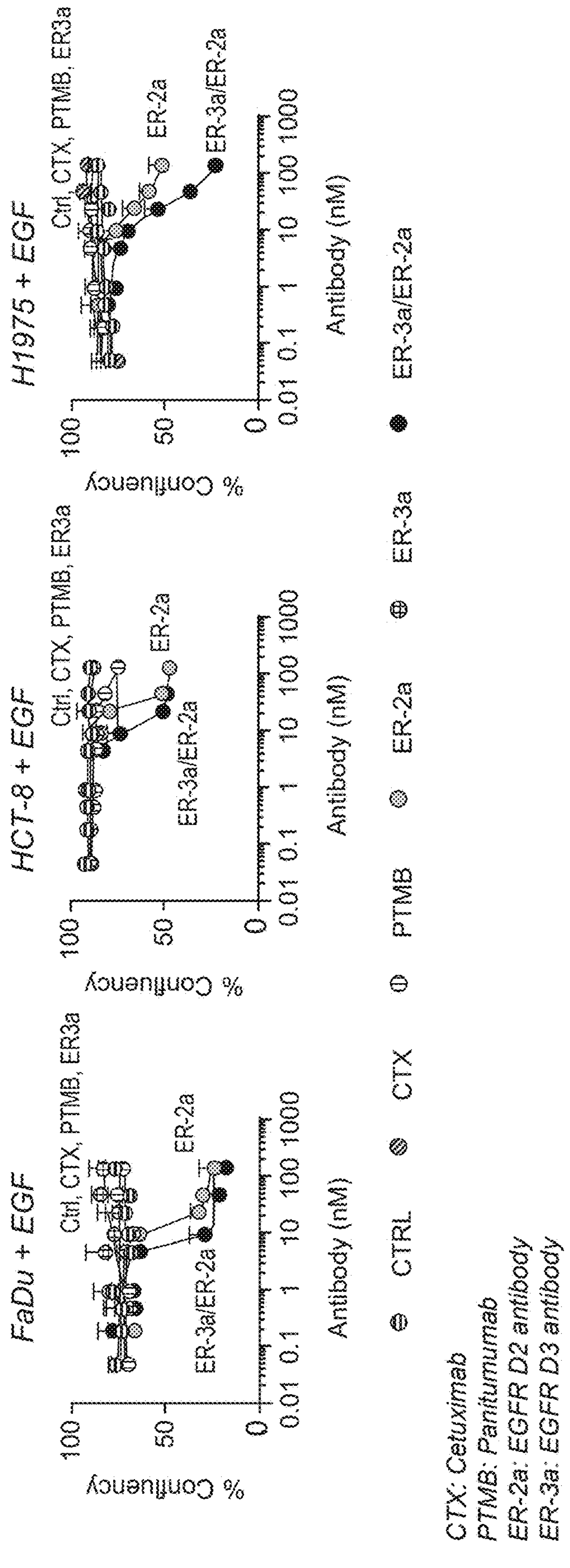
FIG. 4A illustrates inhibition of growth of cell lines in response to EGF using 2a and 3a antibodies alone or combined into a bispecific format, compared to a control or with Cetuximab (CTX) or Panitumumab (PTMB).

A bispecific antibody was made incorporating the binding domains from the ER-3a and ER2a clones. As shown in FIG. 4A the bispecific antibody ER-3a/ER-2a and EGFR active state-binding antibody ER-2a inhibited cell growth in FaDu, an HNSCC cell line, and HCT-8, a CRC cell line, and the NSCLC cell line H1975. FaDu and HCT-8 expressed wild-type EGFR and H1975 expressed EGFR with two kinase domain mutations, L858R and T790M. EGFR's ligand, EGF, was added to these cells to further stimulate EGFR activity and model environments where EGF is expressed. As expected, only the two antibodies that recognized the active state of EGFR, ER-3a/ER-2a, inhibited the proliferation of all three cell lines, as indicated by a reduced confluency percentage.

Figure 4B:
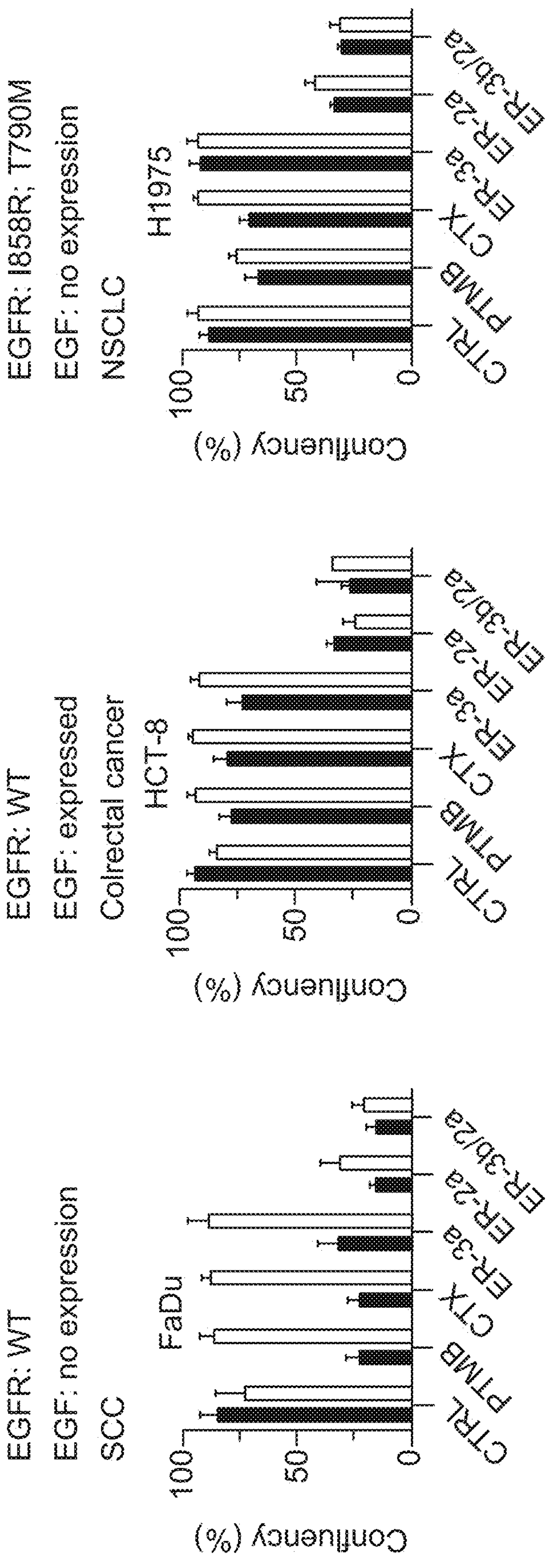
FIG. 4B illustrates inhibition of growth using a bispecific antibody with the binding specificity of 2a and 3a. Without (black bars) or with the presence of EGF (white bars).

As shown in FIG. 4B a bispecific antibody incorporating both the binding domains of 3a and 2a were able to inhibit cell growth in the presence and absence of ligand.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCES

| Seq ID NO | Sequence | Comment |
|---|---|---|
| 1 | MRPSGTAGAALLALLAALCPASRALEEKKVCQGTSNKLTQLGTFEDHFLSLQ<br>RMFNNCEVVLGNLEITYVQRNYDLSFLKTIQEVAGYVLIALNTVERIPLENL<br>QIIRGNMYYENSYALAVLSNYDANKTGLKELPMRNLQEILHGAVRFSNNPAL<br>CNVESIQWRDIVSSDFLSNMSMDFQNHLGSCQKCDPSCPNGSCWGAGEENCQ<br>KLTKIICAQQCSGRCRGKSPSDCCHNQCAAGCTGPRESDCLVCRKFRDEATC<br>KDTCPPLMLYNPTTYQMDVNPEGKYSFGATCVKKCPRNYVVTDHGSCVRACG<br>ADSYEMEEDGVRKCKKCEGPCRKVCNGIGIGEFKDSLSINATNIKHFKNCTS<br>ISGDLHILPVAFRGDSFTHTPPLDPQELDILKTVKEITGFLLIQAWPENRTD<br>LHAFENLEIIRGRTKQHGQFSLAVVSLNITSLGLRSLKEISDGDVIISGNKN<br>LCYANTINWKKLFGTSGQKTKIISNRGENSCKATGQVCHALCSPEGCWGPEP<br>RDCVSCRNVSRGRECVDKCNLLEGEPREFVENSECIQCHPECLPQAMNITCT<br>GRGPDNCIQCAHYIDGPHCVKTCPAGVMGENNTLVWKYADAGHVCHLCHPNC<br>TYGCTGPGLEGCPTNGPKIPSIATGMVGALLLLLVVALGIGLFMRRRHIVRK<br>RTLRRLLQERELVEPLTPSGEAPNQALLRILKETEFKKIKVLGSGAFGTVYK<br>GLWIPEGEKVKIPVAIKELREATSPKANKEILDEAYVMASVDNPHVCRLLGI<br>CLTSTVQLITQLMPFGCLLDYVREHKDNIGSQYLLNWCVQIAKGMNYLEDRR<br>LVHRDLAARNVLVKTPQHVKITDFGLAKLLGAEEKEYHAEGGKVPIKWMALE<br>SILHRIYTHQSDVWSYGVTVWELMTFGSKPYDGIPASEISSILEKGERLPQP<br>PICTIDVYMIMVKCWMIDADSRPKFRELIIEFSKMARDPQRYLVIQGDERMH<br>LPSPTDSNFYRALMDEEDMDDVVDADEYLIPQQGFFSSPSTSRTPLLSSLSA<br>TSNNSTVACIDRNGLQSCPIKEDSFLQRYSSDPTGALTEDSIDDTFLPVPEY<br>INQSVPKRPAGSVQNPVYHNQPLNPAPSRDPHYQDPHSTAVGNPEYLNTVQP<br>TCVNSTFDSPAHWAQKGSHQISLDNPDYQQDFFPKEAKPNGIFKGSTAENAE<br>YLRVAPQSSEFIGA | Human EGFR |
| 2 | DIQMTQSPSSLSASVGDRVTITCRASQDV**N**TAVAWYQQKPGKAPKLLIYSAS<br>FLYSGVPSRFSGSRSGTDFTLTISSLQPEDFATYYCQQHYTTPPTFGQGTKV<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>FNRGEC | Common light chain [N] |
| 3 | DIQMTQSPSSLSASVGDRVTITCRASQDV**S**TAVAWYQQKPGKAPKLLIYSAS<br>FLYSGVPSRFSGSRSGTDFTLTISSLQPEDFATYYCQQHYTTPPTFGQGTKV<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>ENRGEC | Common light chain [S] |
| 4 | DVSTA | CDR-L1 |
| 5 | DVNTA | CDR-L1 |
| 6 | SASFLYS | CDR-L2 |
| 7 | HYTTPP | CDR-L3 |
| 8 | EVQLVESGGGLVQPGGSLRLSCAASGFNLYYSSMHWVRQAPGKGLEWVASIS<br>PYYGYTSYADSVKGRFTISADTSKNTAYLQMNSLRAEDTAVYYCARYYHFSW<br>HWSSFGGSYYPGMDYWGQGTLVTVSS | ER2-VH [N28] |
| 9 | LYYSM | ER2-H1 |
| 10 | SISPYYGYTS | ER2-H2 |
| 11 | YYHFSWHWSSFGGSYYPGM | ER2-H3 |
| 12 | EVQLVESGGGLVQPGGSLRLSCAASGFDVYYAAMHWVRQAPGKGLEWVASIS<br>PYYGYTSYADSVKGRFTISADTSKNTAYLQMNSLRAEDTAVYYCARYYHFSW<br>HWSSFGGSYYPGMDYWGQGTLVTVSS | ER2a-VH [D28] |
| 13 | VYYAAM | ER2a-H1 |
| 14 | SISPYYGYTS | ER2a-H2 |

-continued

SEQUENCES

| Seq ID NO | Sequence | Comment |
|---|---|---|
| 15 | YYHFSWHWSSFGGSYYPGM | ER2a-H3 |
| 16 | EVQLVESGGGLVQPGGSLRLSCAASGFNIYYAAMHWVRQAPGKGLEWVAFIS PYYSYTSYADSVKGRFTISADTSKNTAYLQMNSLRAEDTAVYYCARYFHSSW YESSSPRAYYPGMDYWGQGTLVTVSS | ER2b-VH [N28] |
| 17 | IYYAAM | ER2b-H1 |
| 18 | FISPYYSYTS | ER2b-H2 |
| 19 | YFHSSWYESSSPRAYYPGM | ER2b-H3 |
| 20 | EVQLVESGGGLVQPGGSLRLSCAASGFNIYYAAMHWVRQAPGKGLEWVAFIS PYYSYTSYADSVKGRFTISADTSKNTAYLQMNSLRAEDTAVYYCARYYHISW PWSSYGGTYYPGMDYWGQGTLVTVSS | ER2c-VH [N28] |
| 21 | IYYAAM | ER2c-H1 |
| 22 | FISPYYSYTS | ER2c-H2 |
| 23 | YYHISWPWSSYGGTYYPGM | ER2c-H3 |
| 24 | DYHISWPWSSYGGTYYPGM | ER2c-H3 |
| 25 | YDHISWPWSSYGGTYYPGM | ER2c-H3 |
| 26 | YYDISWPWSSYGGTYYPGM | ER2c-H3 |
| 27 | YYHDSWPWSSYGGTYYPGM | ER2c-H3 |
| 28 | YYHIDWPWSSYGGTYYPGM | ER2c-H3 |
| 29 | YYHISDPWSSYGGTYYPGM | ER2c-H3 |
| 30 | YYHISWDWSSYGGTYYPGM | ER2c-H3 |
| 31 | YYHISWPDSSYGGTYYPGM | ER2c-H3 |
| 32 | YYHISWPWDSYGGTYYPGM | ER2c-H3 |
| 33 | YYHISWPWSDYGGTYYPGM | ER2c-H3 |
| 34 | YYHISWPWSSDGGTYYPGM | ER2c-H3 |
| 35 | YYHISWPWSSYDGTYYPGM | ER2c-H3 |
| 36 | YYHISWPWSSYGDTYYPGM | ER2c-H3 |
| 37 | YFHSSWYESSSPRDYYPGM | ER2c-H3 |
| 38 | YFHSSWYESSSPRAYDPGM | ER2c-H3 |
| 39 | EVQLVESGGGLVQPGGSLRLSCAASGFNLYSYSMHWVRQAPGKGLEWVAYIS PSSGSTYYADSVKGRFTISADTSKNTAYLQMNSLRAEDTAVYYCARHWYYYP SYYWGGFDYWGQGTLVTVSS | ER3-VH |
| 40 | LYSYSM | ER3-H1 |
| 41 | YISPSSGSTY | ER3-H2 |
| 42 | HWYYYPSYYWGGF | ER3-H3 |
| 43 | EVQLVESGGGLVQPGGSLRLSCAASGFDLYSYSMHWVRQAPGKGLEWVASVS PSSGSTYYADSVKGRFTISADTSKNTAYLQMNSLRAEDTAVYYCARHWHVYP SYYWGGFDYWGQGTLVTVSS | ER3a-VH |
| 44 | LYSYSM | ER3a-H1 |
| 45 | SVSPSSGSTY | ER3a-H2 |
| 46 | HVYPSYYWGGF | ER3a-H3 |

-continued

SEQUENCES

| Seq ID NO | Sequence | Comment |
|---|---|---|
| 47 | EVQLVESGGGLVQPGGSLRLSCAASGFDIYSFSIHWVRQAPGKGLEWVASIS<br>PSAGSTYYADSVKGRFTISADTSKNTAYLQMNSLRAEDTAVYYCARHWHVYP<br>SYYWGGMDYWGQGTLVTVSS | ER3b-VH |
| 48 | IYSFSI | ER3b-H1 |
| 49 | SISPSAGSTY | ER3b-H2 |
| 50 | HWHVYPSYYWGGM | ER3b-H3 |
| 51 | EVQLVESGGGLVQPGGSLRLSCAASGFDIYSFSIHWVRQAPGKGLEWVASIS<br>PSAGSTYYADSVKGRFTISADTSKNTAYLQMNSLRAEDTAVYYCARHWHVYP<br>SYYWGGMDYWGQGTLVTVSS | ER3c-VH |
| 52 | IYSFSI | ER3c-H1 |
| 53 | SISPSAGSTY | ER3c-H2 |
| 54 | HDHVYPSYYWGGM | ER3c-H3 |
| 55 | HWHDYPSYYWGGM | ER3c-H3 |
| 56 | HWHVDPSYYWGGM | ER3c-H3 |
| 57 | HWHVYPSDYWGGM | ER3c-H3 |
| 58 | HWHVYPSYYWDGM | ER3c-H3 |
| 59 | HWHVYPSYYWGDM | ER3c-H3 |
| 60 | HWHVYPSYYWGGD | ER3c-H3 |
| 61 | ASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSN<br>KALPAPIEKTISKAKGQPREPMVFDLPPSREEMTKNQVSLWCMVKGFYPSDI<br>AVEWESNGQPENNYKTTPPVLDSDGSFFLYSKLTVDKSRWQQGNVFSCSVMH<br>EALHNHYTQKSLSLSPGK | HC<br>(Knob) |
| 62 | ASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSN<br>KALPAPIEKTISKAKGQPREPQVYTLPPIRELMTSNQVSLSCAVKGFYPSDI<br>AVEWESNGQPENNYKTTPPVLDSDGSFFLVSKLTVDKSRWQQGNVFSCSVMH<br>EALHNHYTQKSLSLSPGK | HC<br>(Hole) |

The invention claimed is:

1. An antibody or antigen binding fragment thereof, comprising an EGFR domain II binding moiety, wherein the EGFR domain II binding moiety comprises:

a) a heavy chain complementarity determining region 1 (HCDR1) comprising an amino acid sequence set forth in SEQ ID NO: 17;

b) a heavy chain complementarity determining region 2 (HCDR2) comprising an amino acid sequence set forth in SEQ ID NO: 18;

c) a heavy chain complementarity determining region 3 (HCDR3) comprising an amino acid sequence set forth in any one of SEQ ID NOs: 19, or 23 to 38;

d) a light chain complementarity determining region 1 (LCDR1) comprising an amino acid sequence set forth in any one of SEQ ID NOs: 4 or 5;

e) a light chain complementarity determining region 2 (LCDR2) comprising an amino acid sequence set forth in SEQ ID NO: 6; and f) a light chain complementarity determining region 3 (LCDR3) comprising an amino acid sequence set forth in SEQ ID NO: 7.

2. The antibody or antigen binding fragment thereof claim 1, wherein the antibody or antigen binding fragment thereof is a bispecific antibody.

3. The antibody or antigen binding fragment thereof of claim 1, wherein the EGFR domain II binding moiety comprises an immunoglobulin light chain, wherein the immunoglobulin light chain comprises an amino acid sequence at least about 90% identical to that set forth in SEQ ID NO: 2 or 3.

4. The antibody or antigen binding fragment thereof of claim 1, wherein the EGFR domain II binding moiety comprises an EGFR domain II binding immunoglobulin heavy chain, wherein the EGFR domain II binding immunoglobulin heavy chain comprises an amino acid sequence at least about 90% identical to that set forth in SEQ ID NO: 16 or 20.

5. An antibody or antigen binding fragment thereof, comprising an EGFR domain III binding moiety, wherein the EGFR domain III antigen binding moiety comprises:

a) a heavy chain complementarity determining region 1 (HCDR1) comprising an amino acid sequence set forth in SEQ ID NO: 52;

b) a heavy chain complementarity determining region 2 (HCDR2) comprising an amino acid sequence set forth in SEQ ID NO: 53;

c) a heavy chain complementarity determining region 3 (HCDR3) comprising an amino acid sequence set forth in any one of SEQ ID NOs: 54 to 60;

d) a light chain complementarity determining region 1 (LCDR1) comprising an amino acid sequence set forth in any one of SEQ ID NOs: 4 or 5;

e) a light chain complementarity determining region 2 (LCDR2) comprising an amino acid sequence set forth in SEQ ID NO: 6; and f) a light chain complementarity determining region 3 (LCDR3) comprising an amino acid sequence set forth in SEQ ID NO: 7.

6. The antibody or antigen binding fragment thereof of claim 5, wherein the antibody or antigen binding fragment thereof is a bispecific antibody.

7. The antibody or antigen binding fragment thereof of claim 5, wherein the EGFR domain III binding moiety comprises an immunoglobulin light chain, wherein the immunoglobulin light chain comprises an amino acid sequence at least about 90% identical to that set forth in SEQ ID NO: 2 or 3.

8. The antibody or antigen binding fragment thereof of claim 5, wherein the EGFR domain III binding moiety comprises an EGFR domain III binding immunoglobulin heavy chain, wherein the EGFR domain III binding immunoglobulin heavy chain comprises an amino acid sequence at least about 90% identical to that set forth in SEQ ID NO: 51.

9. An antibody or antigen binding fragment thereof, wherein the antibody or antigen binding fragment thereof is a multispecific antibody, comprising an EGFR domain II binding moiety and an EGFR domain III binding moiety, wherein the EGFR domain II binding moiety comprises:

a) a heavy chain complementarity determining region 1 (HCDR1) comprising an amino acid sequence set forth in SEQ ID NO: 17;

b) a heavy chain complementarity determining region 2 (HCDR2) comprising an amino acid sequence set forth in SEQ ID NO: 18;

c) a heavy chain complementarity determining region 3 (HCDR3) comprising an amino acid sequence set forth in any one of SEQ ID NOs: 19, or 23 to 38;

d) a light chain complementarity determining region 1 (LCDR1) comprising an amino acid sequence set forth in any one of SEQ ID NOs: 4 or 5;

e) a light chain complementarity determining region 2 (LCDR2) comprising an amino acid sequence set forth in SEQ ID NO: 6; and f) a light chain complementarity determining region 3 (LCDR3) comprising an amino acid sequence set forth in SEQ ID NO: 7;

and wherein the EGFR domain III antigen binding moiety comprises:

g) a heavy chain complementarity determining region 1 (HCDR1) comprising an amino acid sequence set forth in SEQ ID NO: 52;

h) a heavy chain complementarity determining region 2 (HCDR2) comprising an amino acid sequence set forth in SEQ ID NO: 53;

i) a heavy chain complementarity determining region 3 (HCDR3) comprising an amino acid sequence set forth in any one of SEQ ID NOs: 54 to 60;

j) a light chain complementarity determining region 1 (LCDR1) comprising an amino acid sequence set forth in any one of SEQ ID NOs: 4 or 5;

k) a light chain complementarity determining region 2 (LCDR2) comprising an amino acid sequence set forth in SEQ ID NO: 6; and l) a light chain complementarity determining region 3 (LCDR3) comprising an amino acid sequence set forth in SEQ ID NO: 7.

10. The antibody or antigen binding fragment thereof of claim 9, wherein the EGFR domain II binding moiety and the EGFR domain III binding moiety comprises a common immunoglobulin light chain, wherein the common immunoglobulin light chain comprises an amino acid sequence at least about 90% identical to that set forth in SEQ ID NO: 2 or 3.

11. The antibody or antigen binding fragment thereof of claim 9, wherein the EGFR domain II binding moiety comprises an EGFR domain II binding immunoglobulin heavy chain, wherein the EGFR domain II binding immunoglobulin heavy chain comprises an amino acid sequence at least about 90% identical to that set forth in SEQ ID NO: 16 or 20.

12. The antibody or antigen binding fragment thereof of claim 9, wherein the EGFR domain III binding moiety comprises an EGFR domain III binding immunoglobulin heavy chain, wherein the EGFR domain III binding immunoglobulin heavy chain comprises an amino acid sequence at least about 90% identical to that set forth in SEQ ID NO: 51.

13. The antibody or antigen binding fragment thereof of claim 9, wherein the antibody or antigen binding fragment thereof is a bispecific antibody.

14. The antibody or antigen binding fragment thereof of claim 9, wherein the antibody or antigen binding fragment binds to the open conformation of EGFR.

15. A pharmaceutical composition comprising the antibody or antigen binding fragment thereof of claim 1, 5, or 9 and a pharmaceutically acceptable diluent, carrier, or excipient.

16. A nucleic acid or plurality of nucleic acids comprising a polynucleotide sequence encoding the antibody or antigen binding fragment thereof of claim 1, 5, or 9.

17. A cell comprising the nucleic acid or plurality of nucleic acids of claim 16.

18. A method of treating an individual afflicted with a cancer or a tumor comprising administering to the individual afflicted with the cancer or the tumor the antibody or antigen binding fragment thereof of claim 1, 5, or 9, thereby treating the cancer or the tumor.

19. The method of claim 18, wherein the cancer or the tumor expresses EGFR or overexpresses EGFR.

20. The method of claim 18, wherein the cancer or the tumor is a solid tissue cancer.

21. The method of claim 18, wherein the cancer or tumor comprises colorectal cancer, head and neck cancer, or non-small cell lung cancer.

* * * * *

SEQUENCE LISTING

<160> NUMBER OF SEQ ID NOS: 64

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn

-continued

```
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480
```

-continued

```
Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895
```

-continued

Val Trp Ser Tyr Gly Val Thr Val Trp Glu Leu Met Thr Phe Gly Ser
900 905 910

Lys Pro Tyr Asp Gly Ile Pro Ala Ser Glu Ile Ser Ser Ile Leu Glu
915 920 925

Lys Gly Glu Arg Leu Pro Gln Pro Pro Ile Cys Thr Ile Asp Val Tyr
930 935 940

Met Ile Met Val Lys Cys Trp Met Ile Asp Ala Asp Ser Arg Pro Lys
945 950 955 960

Phe Arg Glu Leu Ile Ile Glu Phe Ser Lys Met Ala Arg Asp Pro Gln
965 970 975

Arg Tyr Leu Val Ile Gln Gly Asp Glu Arg Met His Leu Pro Ser Pro
980 985 990

Thr Asp Ser Asn Phe Tyr Arg Ala Leu Met Asp Glu Glu Asp Met Asp
995 1000 1005

Asp Val Val Asp Ala Asp Glu Tyr Leu Ile Pro Gln Gln Gly Phe
1010 1015 1020

Phe Ser Ser Pro Ser Thr Ser Arg Thr Pro Leu Leu Ser Ser Leu
1025 1030 1035

Ser Ala Thr Ser Asn Asn Ser Thr Val Ala Cys Ile Asp Arg Asn
1040 1045 1050

Gly Leu Gln Ser Cys Pro Ile Lys Glu Asp Ser Phe Leu Gln Arg
1055 1060 1065

Tyr Ser Ser Asp Pro Thr Gly Ala Leu Thr Glu Asp Ser Ile Asp
1070 1075 1080

Asp Thr Phe Leu Pro Val Pro Glu Tyr Ile Asn Gln Ser Val Pro
1085 1090 1095

Lys Arg Pro Ala Gly Ser Val Gln Asn Pro Val Tyr His Asn Gln
1100 1105 1110

Pro Leu Asn Pro Ala Pro Ser Arg Asp Pro His Tyr Gln Asp Pro
1115 1120 1125

His Ser Thr Ala Val Gly Asn Pro Glu Tyr Leu Asn Thr Val Gln
1130 1135 1140

Pro Thr Cys Val Asn Ser Thr Phe Asp Ser Pro Ala His Trp Ala
1145 1150 1155

Gln Lys Gly Ser His Gln Ile Ser Leu Asp Asn Pro Asp Tyr Gln
1160 1165 1170

Gln Asp Phe Phe Pro Lys Glu Ala Lys Pro Asn Gly Ile Phe Lys
1175 1180 1185

Gly Ser Thr Ala Glu Asn Ala Glu Tyr Leu Arg Val Ala Pro Gln
1190 1195 1200

Ser Ser Glu Phe Ile Gly Ala
1205 1210

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

```
Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 3
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Val Ser Thr Ala
1               5


<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Val Asn Thr Ala
1               5


<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ala Ser Phe Leu Tyr Ser
1               5


<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Tyr Thr Thr Pro Pro
1               5


<210> SEQ ID NO 8
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
```

```
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Ser Pro Tyr Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr His Phe Ser Trp His Trp Ser Ser Phe Gly Gly Ser
            100                 105                 110

Tyr Tyr Pro Gly Met Asp Tyr Trp Gly Gln Gly Thr Leu Val Thr Val
        115                 120                 125

Ser Ser
    130


<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Tyr Tyr Ser Met
1               5


<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ile Ser Pro Tyr Tyr Gly Tyr Thr Ser
1               5                   10


<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Tyr His Phe Ser Trp His Trp Ser Ser Phe Gly Gly Ser Tyr Tyr
1               5                   10                  15

Pro Gly Met


<210> SEQ ID NO 12
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 12

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asp Val Tyr Tyr Ala
20 25 30

Ala Met His Trp Val Arg Gln Ala Pro Gly Lys Gly Leu Glu Trp Val
35 40 45

Ala Ser Ile Ser Pro Tyr Tyr Gly Tyr Thr Ser Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Tyr Tyr His Phe Ser Trp His Trp Ser Ser Phe Gly Gly Ser
100 105 110

Tyr Tyr Pro Gly Met Asp Tyr Trp Gly Gln Gly Thr Leu Val Thr Val
115 120 125

Ser Ser
130

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Val Tyr Tyr Ala Ala Met
1 5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Ser Ile Ser Pro Tyr Tyr Gly Tyr Thr Ser
1 5 10

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Tyr Tyr His Phe Ser Trp His Trp Ser Ser Phe Gly Gly Ser Tyr Tyr
1 5 10 15

Pro Gly Met

<210> SEQ ID NO 16
<211> LENGTH: 130
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ala
            20                  25                  30

Ala Met His Trp Val Arg Gln Ala Pro Gly Lys Gly Leu Glu Trp Val
        35                  40                  45

Ala Phe Ile Ser Pro Tyr Tyr Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Phe His Ser Ser Trp Tyr Glu Ser Ser Ser Pro Arg Ala
            100                 105                 110

Tyr Tyr Pro Gly Met Asp Tyr Trp Gly Gln Gly Thr Leu Val Thr Val
        115                 120                 125

Ser Ser
    130

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Ile Tyr Tyr Ala Ala Met
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Phe Ile Ser Pro Tyr Tyr Ser Tyr Thr Ser
1               5                   10

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Tyr Phe His Ser Ser Trp Tyr Glu Ser Ser Ser Pro Arg Ala Tyr Tyr
1               5                   10                  15

Pro Gly Met

<210> SEQ ID NO 20
<211> LENGTH: 130

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 20

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Tyr Tyr Ala
20 25 30

Ala Met His Trp Val Arg Gln Ala Pro Gly Lys Gly Leu Glu Trp Val
35 40 45

Ala Phe Ile Ser Pro Tyr Tyr Ser Tyr Thr Ser Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Tyr Tyr His Ile Ser Trp Pro Trp Ser Ser Tyr Gly Gly Thr
100 105 110

Tyr Tyr Pro Gly Met Asp Tyr Trp Gly Gln Gly Thr Leu Val Thr Val
115 120 125

Ser Ser
130

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Ile Tyr Tyr Ala Ala Met
1 5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Phe Ile Ser Pro Tyr Tyr Ser Tyr Thr Ser
1 5 10

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Tyr Tyr His Ile Ser Trp Pro Trp Ser Ser Tyr Gly Gly Thr Tyr Tyr
1 5 10 15

Pro Gly Met

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Asp Tyr His Ile Ser Trp Pro Trp Ser Ser Tyr Gly Gly Thr Tyr Tyr
1 5 10 15

Pro Gly Met

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Tyr Asp His Ile Ser Trp Pro Trp Ser Ser Tyr Gly Gly Thr Tyr Tyr
1 5 10 15

Pro Gly Met

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Tyr Tyr Asp Ile Ser Trp Pro Trp Ser Ser Tyr Gly Gly Thr Tyr Tyr
1 5 10 15

Pro Gly Met

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Tyr Tyr His Asp Ser Trp Pro Trp Ser Ser Tyr Gly Gly Thr Tyr Tyr
1 5 10 15

Pro Gly Met

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Tyr Tyr His Ile Asp Trp Pro Trp Ser Ser Tyr Gly Gly Thr Tyr Tyr
1 5 10 15

Pro Gly Met

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Tyr Tyr His Ile Ser Asp Pro Trp Ser Ser Tyr Gly Gly Thr Tyr Tyr
1 5 10 15

Pro Gly Met

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Tyr Tyr His Ile Ser Trp Asp Trp Ser Ser Tyr Gly Gly Thr Tyr Tyr
1 5 10 15

Pro Gly Met

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Tyr Tyr His Ile Ser Trp Pro Asp Ser Ser Tyr Gly Gly Thr Tyr Tyr
1 5 10 15

Pro Gly Met

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Tyr Tyr His Ile Ser Trp Pro Trp Asp Ser Tyr Gly Gly Thr Tyr Tyr
1 5 10 15

Pro Gly Met

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Tyr Tyr His Ile Ser Trp Pro Trp Ser Asp Tyr Gly Gly Thr Tyr Tyr
1 5 10 15

Pro Gly Met

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

```
Tyr Tyr His Ile Ser Trp Pro Trp Ser Ser Asp Gly Gly Thr Tyr Tyr
1               5                   10                  15

Pro Gly Met
```

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

```
Tyr Tyr His Ile Ser Trp Pro Trp Ser Ser Tyr Asp Gly Thr Tyr Tyr
1               5                   10                  15

Pro Gly Met
```

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

```
Tyr Tyr His Ile Ser Trp Pro Trp Ser Ser Tyr Gly Asp Thr Tyr Tyr
1               5                   10                  15

Pro Gly Met
```

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

```
Tyr Phe His Ser Ser Trp Tyr Glu Ser Ser Ser Pro Arg Asp Tyr Tyr
1               5                   10                  15

Pro Gly Met
```

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

```
Tyr Phe His Ser Ser Trp Tyr Glu Ser Ser Ser Pro Arg Ala Tyr Asp
1               5                   10                  15
```

Pro Gly Met

<210> SEQ ID NO 39
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Tyr
            20                  25                  30

Ser Met His Trp Val Arg Gln Ala Pro Gly Lys Gly Leu Glu Trp Val
        35                  40                  45

Ala Tyr Ile Ser Pro Ser Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Trp Tyr Tyr Tyr Pro Ser Tyr Tyr Trp Gly Gly Phe Asp
            100                 105                 110

Tyr Trp Gly Gln Gly Thr Leu Val Thr Val Ser Ser
        115                 120
```

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

```
Leu Tyr Ser Tyr Ser Met
1               5
```

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

```
Tyr Ile Ser Pro Ser Ser Gly Ser Thr Tyr
1               5                   10
```

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

```
His Trp Tyr Tyr Tyr Pro Ser Tyr Tyr Trp Gly Gly Phe
1               5                   10
```

<210> SEQ ID NO 43
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Tyr Ser Tyr
            20                  25                  30

Ser Met His Trp Val Arg Gln Ala Pro Gly Lys Gly Leu Glu Trp Val
        35                  40                  45

Ala Ser Val Ser Pro Ser Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Trp His Val Tyr Pro Ser Tyr Tyr Trp Gly Gly Phe Asp
            100                 105                 110

Tyr Trp Gly Gln Gly Thr Leu Val Thr Val Ser Ser
        115                 120

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Leu Tyr Ser Tyr Ser Met
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Ser Val Ser Pro Ser Ser Gly Ser Thr Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

His Val Tyr Pro Ser Tyr Tyr Trp Gly Gly Phe
1               5                   10

<210> SEQ ID NO 47
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Ile Tyr Ser Phe
            20                  25                  30

Ser Ile His Trp Val Arg Gln Ala Pro Gly Lys Gly Leu Glu Trp Val
        35                  40                  45

Ala Ser Ile Ser Pro Ser Ala Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Trp His Val Tyr Pro Ser Tyr Tyr Trp Gly Gly Met Asp
            100                 105                 110

Tyr Trp Gly Gln Gly Thr Leu Val Thr Val Ser Ser
        115                 120
```

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

```
Ile Tyr Ser Phe Ser Ile
1               5
```

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

```
Ser Ile Ser Pro Ser Ala Gly Ser Thr Tyr
1               5                   10
```

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

```
His Trp His Val Tyr Pro Ser Tyr Tyr Trp Gly Gly Met
1               5                   10
```

<210> SEQ ID NO 51
<211> LENGTH: 124

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Ile Tyr Ser Phe
            20                  25                  30

Ser Ile His Trp Val Arg Gln Ala Pro Gly Lys Gly Leu Glu Trp Val
        35                  40                  45

Ala Ser Ile Ser Pro Ser Ala Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Trp His Val Tyr Pro Ser Tyr Tyr Trp Gly Gly Met Asp
            100                 105                 110

Tyr Trp Gly Gln Gly Thr Leu Val Thr Val Ser Ser
        115                 120
```

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

```
Ile Tyr Ser Phe Ser Ile
1               5
```

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

```
Ser Ile Ser Pro Ser Ala Gly Ser Thr Tyr
1               5                   10
```

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

```
His Asp His Val Tyr Pro Ser Tyr Tyr Trp Gly Gly Met
1               5                   10
```

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

His Trp His Asp Tyr Pro Ser Tyr Tyr Trp Gly Gly Met
1 5 10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

His Trp His Val Asp Pro Ser Tyr Tyr Trp Gly Gly Met
1 5 10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

His Trp His Val Tyr Pro Ser Asp Tyr Trp Gly Gly Met
1 5 10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

His Trp His Val Tyr Pro Ser Tyr Tyr Trp Asp Gly Met
1 5 10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

His Trp His Val Tyr Pro Ser Tyr Tyr Trp Gly Asp Met
1 5 10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

His Trp His Val Tyr Pro Ser Tyr Tyr Trp Gly Gly Asp
1 5 10

<210> SEQ ID NO 61
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Met Val Phe Asp Leu Pro Pro Ser Arg Glu Glu
225                 230                 235                 240

Met Thr Lys Asn Gln Val Ser Leu Trp Cys Met Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 62
<211> LENGTH: 330
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ile Arg Glu Leu
225                 230                 235                 240

Met Thr Ser Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

```
Leu Tyr Tyr Ser Ser Met
1               5


<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His Trp His Val Tyr Pro Ser Tyr Tyr Trp Gly Gly Phe
1               5                   10
```